(12) United States Patent
Oral et al.

(10) Patent No.: US 10,000,305 B2
(45) Date of Patent: Jun. 19, 2018

(54) ANTIOXIDANT-STABILIZED JOINT IMPLANTS

(71) Applicants: Ebru Oral, Newton, MA (US); Orhun Muratoglu, Cambridge, MA (US)

(72) Inventors: Ebru Oral, Newton, MA (US); Orhun Muratoglu, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 666 days.

(21) Appl. No.: 14/400,375

(22) PCT Filed: May 9, 2013

(86) PCT No.: PCT/US2013/040313
§ 371 (c)(1),
(2) Date: Nov. 11, 2014

(87) PCT Pub. No.: WO2013/170005
PCT Pub. Date: Nov. 14, 2013

(65) Prior Publication Data
US 2015/0151866 A1 Jun. 4, 2015

Related U.S. Application Data

(60) Provisional application No. 61/645,668, filed on May 11, 2012, provisional application No. 61/794,457, filed on Mar. 15, 2013.

(51) Int. Cl.
*A61L 27/16* (2006.01)
*B65B 55/16* (2006.01)
*A61L 27/50* (2006.01)
*C08L 23/06* (2006.01)
*C08J 7/12* (2006.01)
*A61F 2/30* (2006.01)

(52) U.S. Cl.
CPC ............ *B65B 55/16* (2013.01); *A61F 2/30* (2013.01); *A61L 27/16* (2013.01); *A61L 27/50* (2013.01); *C08J 7/123* (2013.01); *C08L 23/06* (2013.01); *A61F 2240/001* (2013.01); *A61L 2300/428* (2013.01); *C08J 2323/06* (2013.01); *C08L 2207/068* (2013.01)

(58) Field of Classification Search
CPC ........ A61K 27/16; A61K 27/00; A61K 27/50; C08J 7/123; C08L 23/06
See application file for complete search history.

(56) References Cited

U.S. PATENT DOCUMENTS 8,293,811 B2 * 10/2012 Muratoglu ............ C08F 10/02
522/111
2010/0190882 A1 7/2010 Muratoglu et al.

FOREIGN PATENT DOCUMENTS

WO WO 9729793 A1 * 8/1997 ............ A61F 2/32

OTHER PUBLICATIONS

International Search Report dated Oct. 2, 2013, in connection with PCT/US2013/040313.
Gall, D., et al. Electron Scattering in Narrow Metal Wires. Interconnect Technology Conference, 2006, abstract.

* cited by examiner

*Primary Examiner* — Sanza Mcclendon
(74) *Attorney, Agent, or Firm* — Quarles & Brady LLP

(57) ABSTRACT

Methods of making a wear and oxidation resistant medical implant are disclosed.

35 Claims, 27 Drawing Sheets

| Cradle Row # | Irradiation Dose | -3 | -2 | -1 | 0 | + 1 | + 2 | + 3 |
|---|---|---|---|---|---|---|---|---|
| 6 | 170 kGy |  | E - 7 (Flat) | E - 8 (Flat) | E - 9 (Flat) |  |  |  |
| 5 | 160 kGy |  |  |  | E - 4 (Flat) | E - 5 (Flat) | E - 6 (Flat) |  |
| 4 | 150 kGy | E - 1 (Flat) |  | 38Ø - M - 2 (Round) | E - 2 (Flat) |  | 38Ø - M - 1 (Flat) | E - 3 (Flat) |
| 3 | 150 kGy | 38Ø - 1 | 38Ø - 2 | 38Ø - 3 | 38Ø - 4 | 38Ø - 5 | 38Ø - 6 | 38Ø - 7 |
| 2 | 150 kGy | 34Ø - 1 | 34Ø - 2 | 34Ø - 3 | 34Ø - 4 | 34Ø - 5 | 34Ø - 6 | 34Ø - 7 |
| 1 | 150 kGy | Control-1 (Flat) | Control-2 (Flat) | 34Ø - M - 2 (Round) | Control-3 (Flat) | Control-4 (Flat) | 34Ø - M - 1 (Flat) | Control-5 (Flat) |

Figure 24

ANTIOXIDANT-STABILIZED JOINT IMPLANTS

CROSS-REFERENCES TO RELATED APPLICATIONS

This application is a 371 application of PCT/US2013/040313 filed May 9, 2013 which claims priority from U.S. Provisional Patent Application No. 61/645,668, filed May 11, 2012, and U.S. Provisional Patent Application No. 61/794,457, filed Mar. 15, 2013.

STATEMENT REGARDING FEDERALLY SPONSORED RESEARCH

Not Applicable.

BACKGROUND OF THE INVENTION

1. Field of the Invention

The present invention relates to methods for making wear resistant polymeric materials. Methods of making medical implants containing antioxidant-containing wear resistant polymers and materials used therewith also are provided. Wear resistant polymeric materials and medical implants containing such materials are also provided.

2. Description of the Related Art

It is advantageous to have tough and ductile polymeric materials, for example, ultrahigh molecular weight polyethylene (UHMWPE), for total joint implants without sacrificing oxidative stability and wear resistance. Wear resistance can be improved by cross-linking. However, crosslinking reduces the toughness and ductility of the material. Therefore, it is desirable to have a method to increase toughness and ductility of wear and oxidation resistant polymeric material.

Antioxidant stabilization of various cross-linked polyethylenes has been described. Schaffner (U.S. Pat. No. 6,277,390) described a disperse formulation of UHMWPE blended with vitamin E as an antioxidant and sterilized by ionizing irradiation, but he did not disclose any information neither on a UHMWPE formulation protected against oxidation in the long term nor one that has a limited crosslinking on the surface. McKellop (U.S. Pat. No. 6,494,917) described methods of low energy irradiation to limit cross-linking on the surface but he did not disclose neither methods of making highly oxidation resistant polymeric material by antioxidants nor methods of making antioxidant-stabilized materials. Lindgren (U.S. Pat. No. 6,448,315) described methods of blending UHMWPE with antioxidant and further gamma irradiation but did not disclose methods of low energy irradiation nor other methods of antioxidant incorporation after irradiation. Muratoglu (U.S. Pat. No. 7,431,874) disclosed methods of making antioxidant-stabilized materials by doping polymeric material with antioxidants after radiation crosslinking but taught against the inclusion of the antioxidant before cross-linking.

SUMMARY OF THE INVENTION

The present invention describes a combination of the antioxidant blending, radiation crosslinking and diffusion methods described here which enable the formulation of a highly wear resistant, highly oxidation resistant UHMWPE formulation for total joint implants with improved mechanical properties.

This invention pertains to making oxidation resistant polymers with spatially controlled crosslinking using methods of irradiation.

Antioxidants such as vitamin E or alpha-tocopherol can hinder radiation cross-linking of polymers. Thus, a spatially controlled profile of crosslink density in a polymer can be obtained by controlling the antioxidant concentration in the polymer before/during irradiation. Another option is to manipulate irradiation parameters and methods to spatially control crosslinking.

In one aspect of this invention, an antioxidant-blended polyethylene is irradiated with electron beam irradiation using low energy electrons, for example 1 MeV. The electron penetration into the polymer from the incident surface of the beam can be controlled by the beam energy (see FIG. 1).

Typical accelerators used in the manufacture of joint implants use electrons with 5-10 MeV energy. Accelerators which use direct current can produce a consistent stream of low energy (<3 MeV) electrons which can be used with a scan horn (see FIG. 1). Typically, the samples of interest travel under the scan horn on a conveying system repeated a number of times to reach the desired total dose of irradiation. The dose rate that can be applied to a sample decreases generally with electron energy and can be modified slightly by increasing beam current.

The scatter of electrons before the electrons reach the material to be irradiated can vary depending on the environment and the beam energy. Thus, the distance of the sample from the electron source and the angle of incidence of the electrons relative to the curvature of the surface can make large differences in the electron dose received by the material and can affect the amount of cross-linking spatially. These effects can be heightened when the energy of the incident electrons is low. This invention describes methods of distributing electrons in a controlled manner over the surface of the irradiated polymeric materials when using low energy electrons.

The crosslinking profile can be measured roughly by the calculation of a transvinylene index (TVI; indication of intrachain double bonds formed on the polymer) as measured by Fourier Transform Infrared Spectroscopy (FTIR; see Muratoglu et al., *J Biomed Mater Res* 56: 584-592 (2001)). In UHMWPE, the TVI correlates well with cross-link density (see FIG. 2); therefore, the spatial distribution of crosslinking can be measured by measuring TVI through the depth of the sample.

In one embodiment, a compression molded component made from antioxidant-containing polymeric material is irradiated using low energy radiation thereby forming a component with spatially controlled crosslink density with high crosslink density in the surface.

When an antioxidant such as vitamin E is present in polymeric material during irradiation, it can hinder cross-linking in the polymeric material by scavenging the free radicals generated by radiation on the polymer chains. At the same time, some of the antioxidant can get grafted onto the polymer chains, thereby preventing the elution of the antioxidant from the polymer matrix. However, the antioxidant is consumed partially or completely during irradiation, which may decrease the oxidation resistance of the antioxidant-blended, irradiated polymeric material in its intended long-term uses. Thus, it may be desirable to prevent oxidation in the polymeric material during irradiation using a certain concentration of antioxidant in the polymeric material during irradiation, but not to hinder cross-linking very significantly. To increase oxidative stability after the irradiation and to make up for the activity of the consumed antioxidant, more antioxidant can be introduced into the irradiated antioxidant-blended UHMWPE by diffusion.

If a virgin (no antioxidant) polymeric material is diffused with antioxidant after irradiation, the polymeric material is not oxidation resistant until the antioxidant is diffused throughout a consolidated polymeric material or medical implant preform (see Oral et al., "The effect of doping conditions on α-tocopherol stabilized irradiated UHM-WPE", *Transactions of the Annual Meeting of the Orthopaedic Society,* 1673 (2005)). If the polymeric material contains an antioxidant before and during irradiation, it is oxidation resistant throughout its life in manufacturing, on the shelf, and during in vivo medical device service. In addition, a polymeric material, where crosslinking is only desired in the surface (for example, the first 2 mm.) of the consolidated polymeric material or medical implant preform cannot be irradiated without an antioxidant because oxidation of the polymeric material on the surface would occur during irradiation. Therefore, the presence of the antioxidant during irradiation enables the use of technologies which cause crosslinking only on the surface or preferentially on the surface of the irradiated polymeric material, for example, the use of low energy electrons for surface crosslinking such that the surface is not oxidized during manufacturing and irradiation.

Oxidation resistance during the shelf life and in vivo medical device service of the polymeric material can be improved by introducing more antioxidant to the surface of the polymeric material by (1) diffusing antioxidant in the bulk of the polymeric material not consumed by low energy irradiation limited to the surface, or by (2) diffusing antioxidant into the surface from the outside.

In one embodiment, a compression molded component made from antioxidant-containing polymeric material is irradiated using low energy radiation. Then, the component is contacted with an antioxidant to diffuse more antioxidant on the irradiated surface(s) of the component.

In one embodiment, a compression molded component made from antioxidant-containing polymeric material is irradiated using low energy radiation. Then, the component is contacted with an antioxidant to diffuse more antioxidant on the irradiated surface(s) of the component. Then, the antioxidant-diffused irradiated material is heated to homogenize the antioxidant concentration through the polymeric material. The said heating could be at below or above the melting point of the irradiated blend.

In one embodiment, a compression molded component made from antioxidant-containing polymeric material is irradiated using low energy radiation. Then, the irradiated material is heated to homogenize the antioxidant concentration.

It may be desirable to cause grafting or increased entanglement of the antioxidants on/with the polymer chains at least in the surfaces of the implants to prevent or hinder elution of the antioxidant in the long-term from implant surfaces. It may also be desirable to cross-link more than the articular surfaces of the implants, for example, the backside surface of the implants may be cross-linked by low energy irradiation to prevent elution and to cross-link those surfaces. In such embodiments, a compression molded component, material, preform, or implant can be irradiated on opposite surfaces with low energy irradiation to achieve surface crosslinking of the articular surface and the back surface of the subsequently machined implant—if the irradiated article is an implant, it may need no further machining after irradiation or very minor machining.

In some embodiments, a polymeric material is blended with one or more antioxidant(s). The blended polymeric material is consolidated into a medical implant preform or is consolidated into stock, which is then machined into a medical implant preform or an implant. The medical implant preform is irradiated with the electron beam incident to its surface(s) closest to the intended articular surface(s). Then the implant preform is rotated and is irradiated with the electron beam incident to its surface(s) closest to the intended backside surface(s). Then, the component is contacted with an antioxidant to diffuse more antioxidant on the irradiated surface(s) of the component. Then, the antioxidant-diffused irradiated material is optionally heated to homogenize the antioxidant concentration through the polymeric material. Another optional step after the diffusion of the antioxidant step is to irradiate the polymeric material again using low energy electron beam or high energy electron beam. Then, the medical implant preform is machined to form a medical implant. The medical implant is then packaged, and sterilized by gamma sterilization or by gas sterilization such as ethylene oxide or gas plasma sterilization. The final gamma sterilization may serve two purposes, one is to sterilize the implant and the other to graft the antioxidant that was diffused after the surface crosslinking and minimize its elution.

In one aspect, the invention provides a method of making a wear and oxidation resistant medical implant. The method includes the steps of: (a) blending a polymeric material with one or more antioxidant(s); (b) consolidating the blended polymeric material into a medical implant preform; (c) irradiating the medical implant preform with low energy electrons at below 2 MeV with the desired surfaces exposed to the beam; (d) machining the medical implant preform into a medical implant; and (e) packaging and sterilizing the medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) irradiating the medical implant preform with low energy electrons at below 2 MeV with the desired surfaces exposed to the beam with an electron scattering device comprising fibers in contact with or close to the surface to be irradiated; (d) machining the medical implant preform into a medical implant; and (e) packaging and sterilizing the medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) irradiating the medical implant preform with low energy electrons at below 2 MeV with the desired surfaces exposed to the beam with a electron scattering device comprising fibers in contact with or close to the surface to be irradiated; (d) annealing the irradiated medical implant preform; (e) machining the medical implant preform into a medical implant; and (f) packaging and sterilizing the medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) heating the consolidated blended polymeric material; (d) cooling the consolidated blended polymeric material; (e) irradiating the medical implant preform with low energy electrons at below 2 MeV with the desired surfaces exposed to the beam with a electron scattering device comprising fibers in contact with or close to the surface to be irradiated; (f) machining the medical implant preform into a medical implant; and (g) packaging and sterilizing the medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) high pressure crystallizing the blended polymeric material; (d) cooling the consolidated blended polymeric material; (e) irradiating the medical implant preform with low energy electrons at below 2 MeV with the desired surfaces exposed to the beam with a electron scattering device comprising fibers in contact with or close to the surface to be irradiated (f) machining the medical implant preform into a medical implant; and (g) packaging and sterilizing the medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant; (c) irradiating the medical implant preform with low energy electrons at below 2 MeV with the desired surfaces exposed to the beam with an electron scattering device comprising fibers in contact with or close to the surface to be irradiated; and (d) packaging and sterilizing the medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) irradiating the medical implant preform with low energy electrons at below 2 MeV with the desired surfaces exposed to the beam; (d) annealing the medical implant preform at a temperature below or above the melt; and (e) machining the medical implant preform into a medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) irradiating the medical implant preform with low energy electrons at below 2 MeV with the desired surfaces exposed to the beam; (d) doping the medical implant preform with one or more antioxidant(s); and (e) machining the medical implant preform into a medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) irradiating the medical implant preform with low energy electrons at below 2 MeV with the desired surfaces exposed to the beam; (d) doping the medical implant preform with one or more antioxidant(s); (e) annealing the medical implant preform at a temperature below or above the melt; and (f) machining the medical implant preform into a medical implant.

In another aspect, the invention provides a method of making a wear and oxidation resistant medical implant. The method includes the steps of: (a) blending a polymeric material with one or more antioxidant(s); (b) consolidating the blended polymeric material into a medical implant preform; (c) irradiating the medical implant preform with low energy electrons at below 2 MeV, wherein the surfaces to be irradiated are situated at an angle such that the electrons are incident at a normal to the surface; (d) machining the medical implant preform into a medical implant; and (e) packaging and sterilizing the medical implant.

In the method, the antioxidant used in blending in and doping/diffusion can be vitamin E.

In the method, the material can be pre-heated to an elevated temperature before irradiation such that the material is irradiated between 100° C. and 130° C.

In the method, the antioxidant concentration in the blend can be 0.1 wt %. In the method, the antioxidant concentration in the blend can be 0.3 wt %.

In the method, the irradiation can be an electron beam irradiation.

In the method, the irradiation dose can be 125 kGy. In the method, the irradiation dose can be 200 kGy. In the method, the radiation dose rate can be between about 1 kGy/pass to 50 kGy/pass. In the method, the radiation dose can be about 5 kGy/pass or 25 kGy/pass.

In the method, the electron beam energy can be between about 1 and 4 MeV. In the method, the electron beam energy can be 1.7 MeV.

In the method, the sterilization can be a gamma sterilization.

In the method, the electron scattering device can be made of metallic fibers. In the method, the electron scattering device can be made of metallic wool. In the method, the electron scattering device can be made of metallic brushes.

In the method, the electron scattering device can be situated within a millimeter of the intended surfaces to be irradiated. In the method, the electron scattering device can be situated within thirty centimeters of the intended surfaces to be irradiated.

These and other features, aspects, and advantages of the present invention will become better understood upon consideration of the following detailed description, drawings, and appended claims.

BRIEF DESCRIPTION OF THE DRAWINGS

FIG. 24 shows the layout of the hemispherical recessed and flat samples on the irradiation 'cradle' of FIG. 23. The travel direction is 1→6. Samples labeled with 'E' were 0.1 wt % vitamin E blended, samples labeled control did not have vitamin E. The hemispherical recessed samples were irradiated in rows 2 and 3. Flat control samples without recess were irradiated in row 1.

DETAILED DESCRIPTION OF THE INVENTION

Irradiation

Figure 1:
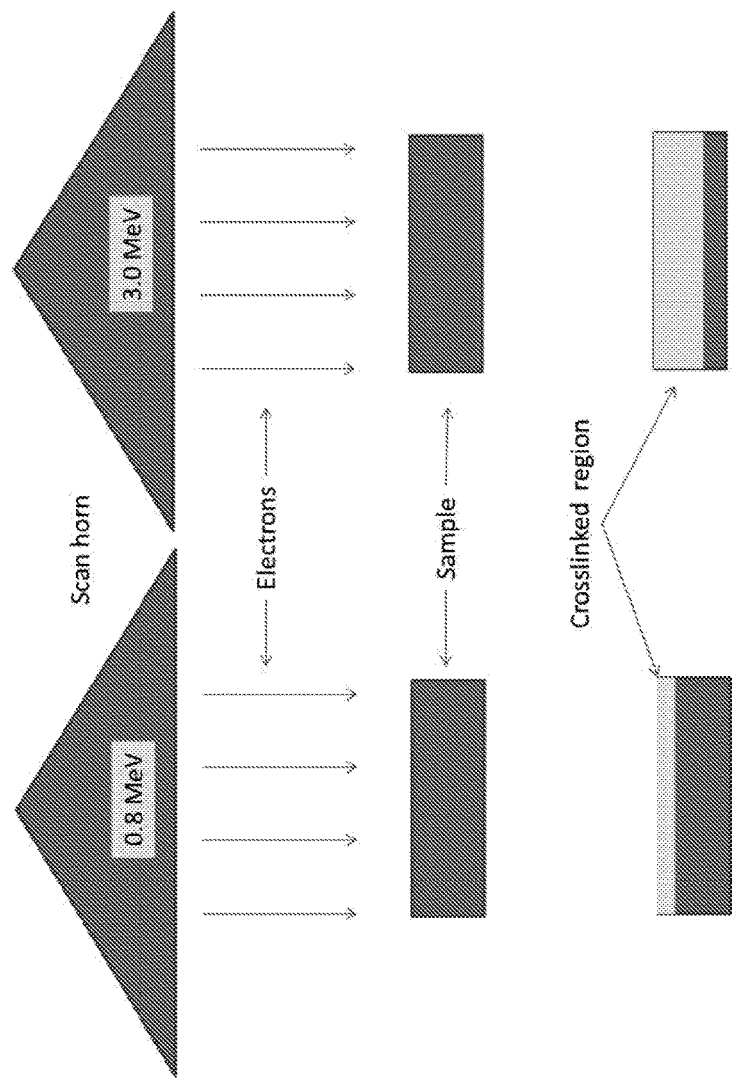
FIG. 1 is a schematic of the depth of crosslinking in a polymer after being irradiated at different electron beam energy.
Figure 2:
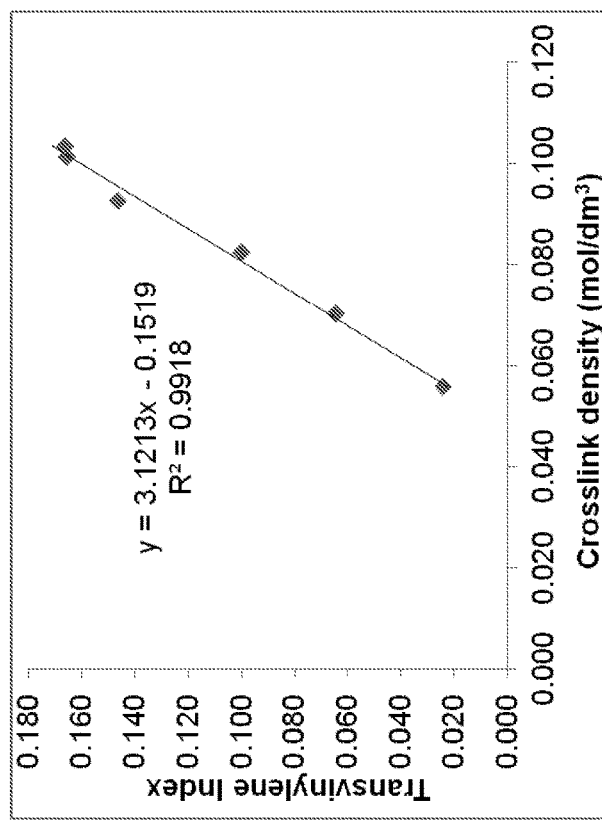
FIG. 2 shows transvinylene index as a function of cross-link density for electron beam irradiated 1 wt % vitamin E-blended UHMWPE at room temperature.

"Irradiation", in one aspect of the invention, the type of radiation, preferably ionizing, is used. For the purposes of cross-linking the polymeric materials in this invention, a dose of ionizing radiation ranging from about 25 kGy to about 1000 kGy is used. The radiation dose can be about 25 kGy, about 50 kGy, about 65 kGy, about 75 kGy, about 100 kGy, about 150, kGy, about 200 kGy, about 300 kGy, about 400 kGy, about 500 kGy, about 600 kGy, about 700 kGy, about 800 kGy, about 900 kGy, or about 1000 kGy, or above 1000 kGy, or any value thereabout or therebetween. Preferably, the radiation dose can be between about 25 kGy and about 150 kGy or between about 50 kGy and about 100 kGy.

According to an aspect of this invention, for cross-linking purposes, the depth to which there is cross-linking in the polymeric material is controlled by the energy of the radiation used. Electron irradiation, in general, results in a more limited dose penetration depth. The penetration of the electron beam depends on the beam energy measured by million electron-volts (MeV). Most polymers exhibit a density of about 1 g/cm$^3$, which leads to a penetration of about 3 mm with a beam energy of 1-1.5 MeV, about 1 cm with a beam energy of 2-3 MeV and about 4 cm with a beam energy of 10 MeV. The penetration of e-beam is known to increase slightly with increased irradiation temperatures. According to this invention, the desired depth of penetration is adjusted based on the beam energy. Electron beam energy of less than 1.5 MeV is preferred to limit the cross-linking to the surface 3 mm of the irradiated polymeric material. There is also a cascade effect with electrons penetrating the polymer: The absorbed dose, that is the radiation dose absorbed by the material, increasing with depth away from the e-beam incident surface, reaches a maximum and then declines rapidly with depth. The e-beam penetration depth usually describes the iso-dose penetration depth; that is the depth at which the declining absorbed dose equals the incident dose at the surface.

For purposes of sterilizing the polymeric materials in this invention, ionizing radiation, including gamma, x-ray, and/or electron beam, can kill or inactivate bacteria, viruses, or other microbial agents potentially contaminating medical implants, including the interfaces, thereby achieving product sterility.

Irradiation for crosslinking or sterilization, in accordance with the present invention can be carried out in air atmosphere containing oxygen, wherein the oxygen concentration in the atmosphere is at least 1%, 2%, 4%, or up to about 22%, or any value thereabout or therebetween. In another aspect, the irradiation can be carried out in an inert atmosphere, wherein the atmosphere contains gas selected from the group consisting of nitrogen, argon, helium, neon, or the like, or a combination thereof. The irradiation also can be carried out in a sensitizing gas such as acetylene or mixture or a sensitizing gas with an inert gas or inert gases. The irradiation also can be carried out in a vacuum, for instance in vacuum sealed packaging.

The irradiation can also be carried out at room temperature, or at between room temperature and the melting point of the polymeric material, or at above the melting point of the polymeric material. The irradiation can be carried out at any temperature or at any dose rate. The polymer can be first heated and then irradiated. Alternatively, the heat generated by the beam, i.e., radiation generated heating (including adiabatic and partially adiabatic) can increase the temperature of the polymer. Alternatively, the polymer can be actively heated during irradiation, for example, in a heating basket or an oven, which can be accommodated on the belt/tracks of the radiation environment.

Subsequent to irradiation for cross-linking, the polymer can be heated to melt or heated to a temperature below its melting point for annealing. These post-irradiation thermal treatments can be carried out in air, inert gas and/or in vacuum. Also the irradiation can be carried out in small increments of radiation dose and in some embodiments these sequences of incremental irradiation can be interrupted with a thermal treatment. The sequential irradiation can be carried out with about 1, 10, 20, 30, 40, 50, 100 kGy, or higher radiation dose increments. Between each or some of the increments the polymer can be thermally treated by melting and/or annealing steps. The thermal treatment after irradiation is mostly to reduce or to eliminate the residual free radicals in the polymers created by irradiation, and/or eliminate the crystalline matter, and/or help in the removal of any extractables that may be present in the polymer.

In accordance with the invention, the irradiation for crosslinking may be carried out in a sensitizing atmosphere. This may comprise a gaseous substance which is of sufficiently small molecular size to diffuse into the polymer and which, on irradiation, acts as a polyfunctional grafting moiety. Examples include substituted or unsubstituted polyunsaturated hydrocarbons; for example, acetylenic hydrocarbons such as acetylene; conjugated or unconjugated olefinic hydrocarbons such as butadiene and (meth)acrylate monomers; sulphur monochloride, with chloro-tri-fluoroethylene (CTFE) or acetylene being particularly preferred. By "gaseous" is meant herein that the sensitizing atmosphere is in the gas phase at the irradiation temperature.

The polymeric material is a polymer in the form of powder. The polymeric material can also be in the consolidated form of the polymeric powder; the consolidation can be achieved at any temperature and pressure. The polymeric material can also be machined after consolidation to any shape, such as an article, an implant preform, or an implant. The implant preform is a shape that is very close to the intended final implant shape. The implant will be machined after any of the subsequent steps of processing to the final implant shape. If the polymeric material is in the implant shape, it will not need any further machining with the exception of some minor machining after any of the subsequent processing steps—for instance to create the locking features needed to secure the implant to the intended metallic component that will mate with bone in vivo. The implant could also be directly fixed to bone with the use of bone cement or a similar surgical adhesive. The polymeric material could contain no antioxidants or it could contain one or more antioxidants.

The term "dose rate" refers to a rate at which the radiation is carried out. Dose rate can be controlled in a number of ways, for instance by changing the power of the electron beam, scan width, conveyor speed, and/or the distance between the sample and the scan horn. Another way is by carrying out the irradiation in multiple passes with, if desired, cooling or heating steps in-between. With gamma and x-ray radiations, the dose rate is controlled by how close the sample is to the radiation source, how intense is the source, the speed at which the sample passes by the source.

Gamma irradiation, however, generally provides low radiation dose rate and requires a longer duration of time, which can result in more in-depth oxidation, particularly if the gamma irradiation is carried out in air. Electron irradiation, in general, results in a more limited dose penetration depth, but requires less time and, therefore, reduces the risk of extensive oxidation if the irradiation is carried out in air. In addition, if the desired dose levels are high, for instance 20 MRad, the irradiation with gamma may take place over one day, leading to impractical production times. On the other hand, the dose rate of the electron beam can be adjusted by varying the irradiation parameters, such as conveyor speed, scan width, and/or beam power. With the appropriate parameters, a 20 MRad irradiation can be completed in for instance less than 10 minutes. Accordingly, gamma irradiation or electron irradiation may be used based upon the depth of penetration preferred, time limitations and tolerable oxidation levels.

Ranges of acceptable dose rates are exemplified in PCT International Application Publication No. WO 97/29793. In general, the dose rates vary between 0.5 MRad/pass and 50 MRad/pass. The upper limit of the dose rate depends on the beam energy, sample configuration such as distance from the radiation source and resistance of the polymer to cavitation/cracking induced by the irradiation. The dose rate can be 0.0001 MRad/pass to the total dose in a single pass. It can be 1 kGy/pass to 250 kGy/pass or more in 1 kGy intervals.

If electron beam irradiation is utilized, the energy of the electrons also is a parameter that can be varied to tailor the properties of the irradiated polymer. In particular, differing electron energies result in different depths of penetration of the electrons into the polymer. The practical electron energies range from about 0.1 MeV to 16 MeV giving approximate iso-dose penetration depths of 0.5 mm to 8 cm, respectively. The preferred electron energy for this invention is about 1-4 MeV, which is commercially available through vendors such as E-Beam Services (New Jersey, USA). The lower electron energies is preferred for embodiments where a surface layer of the polymer is preferentially cross-linked with gradient in cross-link density as a function of distance away from the surface. The polymeric material can also be e-beam irradiated with higher energy e-beam (e.g. 5, 10, and 16 MeV) whereby the polymeric material is sufficiently thick to allow for subsequent machining to limit the resulting crosslinking to a thin surface layer of the final implant.

In accordance with another aspect of the invention, the polymeric preform also has a gradient of cross-link density in a direction perpendicular to the direction of irradiation, wherein a part of the polymeric preform was preferentially shielded to partially block radiation during irradiation in order to provide the gradient of cross-link density, wherein the preferential shielding is used where a gradient of cross-link density is desired and the gradient of cross-link density is in a direction perpendicular to the direction of irradiation on the preferentially shielded polymeric preform, such as is disclosed in U.S. Pat. No. 7,205,339, the methodologies of which are hereby incorporated by reference.

The selective, controlled manipulation of polymers using radiation chemistry can, in another aspect, be achieved by preferential irradiation shielding. By using a shield or shields made of selected materials, selected thicknesses, selected geometries, selected areas and utilization of the shields in a selected order, the overall properties of the irradiated polymer may be controlled and tailored to achieve a desired result, particularly in view of alterations that can be made in the type of irradiation, the irradiation dose, dose rate and exposure time and temperature, as well as the methodology used (for example, irradiation below or above the melt).

Another method of achieving surface crosslinking is by the use of any energy electron beam but with a shield placed between the polymeric material to be irradiated and the beam. The beam is incident to the shield. The density of the shield material and/or the thickness of the shield is varied to reduce the beam energy to the desired level and thus control the depth of penetration. The shield can serve two purposes: (1) To control the depth of penetration of the effect of e-beam on the polymeric material, for instance to achieve surface crosslinking. (2) To prevent the crosslinking of the polymeric material in regions where the crosslinking is not desirable, for instance the non-articular surfaces where the locking features are located.

To achieve the optimum properties of high cross-linking on the surface and low/no cross-linking in the bulk (improved mechanical properties) for UHMWPE, it is desirable to have as sharp of a transition from the high radiation exposure to the low radiation exposure. This can be achieved by using lower electron beam energies of irradiation but also can be enhanced by using different shield materials. A shield made out of a heavier atom or atoms will absorb more radiation energy. Therefore, changing the type and thickness of the shield material, a desired gradient interface thickness can be achieved at the desired depth from the surfaces closest to the radiation source. Examples of how radiation dose, beam power, irradiation temperature, and shield thickness can change the radiation penetration depth using electron-beam irradiation of UHMWPE are described in Muratoglu et al., *J Biomed Mater Res* 56:584-592 (2001) and U.S. Patent Application Publication No. 2004/0051213 A1.

a. Shield Material

The irradiation shield may be made from any material that will at least shield in part polymer from the irradiation. Exemplary materials include ceramics, metals, and glass. Suitable ceramics include alumina and zirconia. Suitable metals include aluminum, copper, lead, iron, and steel. Polymers also may be used as shields.

b. Shield Geometries and Order

An irradiation shield may be provided in any shape, cross-section, or thickness.

It is well known in the art that the thickness of the shield will contribute to the ability of the material to shield the irradiation. Accordingly, the thickness of the shield can be selected depending upon the extent of shielding that is desired in the shielded portion. In this manner, the depth of irradiation penetration can be controlled, or a total shielding of irradiation of the covered areas can be achieved. The iso-dose penetration (defined as the depth at which the dose equals that at the e-beam incidence surface) and the dose-depth penetration profile depend on the energy of the electrons used.

The irradiation of materials with electrons leads to the well-known build-up of absorbed dose level as a function of distance away from the electron beam incidence surface. This built-up of the absorbed dose is due to the generation of secondary electrons following the collision of the incident electrons with the atoms of the host material. This build up can occur to a larger extent in non-conductors and may not occur in good conductors of electrons. The collisions generate more electrons at the expense of losing kinetic energy while increasing the effective absorbed dose level as the electron flux travels into the material. At a critical depth, the kinetic energy loss reaches a level where the electron flux slows down and leads to an abrupt decay in the absorbed dose level. The depth at which the absorbed dose level is equal to that at the surface is called the iso-dose penetration depth. This penetration increases with the increasing energy of the incident electrons. Dosimetry and/or determination of trans-vinylene unsaturations can be used to determine the iso-dose penetration or penetration of the radiation in general.

Thus, the effect of irradiation and shielding can be controlled through the materials used in the shield, the thickness of the shield (constant or variable), the extent to which the shield covers the area of the material being irradiated (full or partial), the order of shielding and irradiation, the type and extent of irradiation, and polymer selection.

c. Complete Coverage Shielding

UHMWPE (GUR 1050) was covered by an aluminum shield of varying thicknesses (1, 3, 5, 7, 9, 11, 13, 15 mm) and irradiated either at room temperature or at 125° C. The irradiation was carried out at E-Beam Services (Cranbury, N.J.) using the 10/50 Impela linear electron accelerator operated at 10 MeV and 50 kW. To determine the penetration profile of the effects of e-beam, spatial variation in the trans-vinylene content in the irradiated UHMWPE specimens was determined. The GUR 1050 UHMWPE has no detectable trans-vinylene unsaturations. The ionizing radiation, e-beam in the present case, led to the formation of trans-vinylene unsaturations, the content of which varied linearly with absorbed radiation dose.

Figure 3:
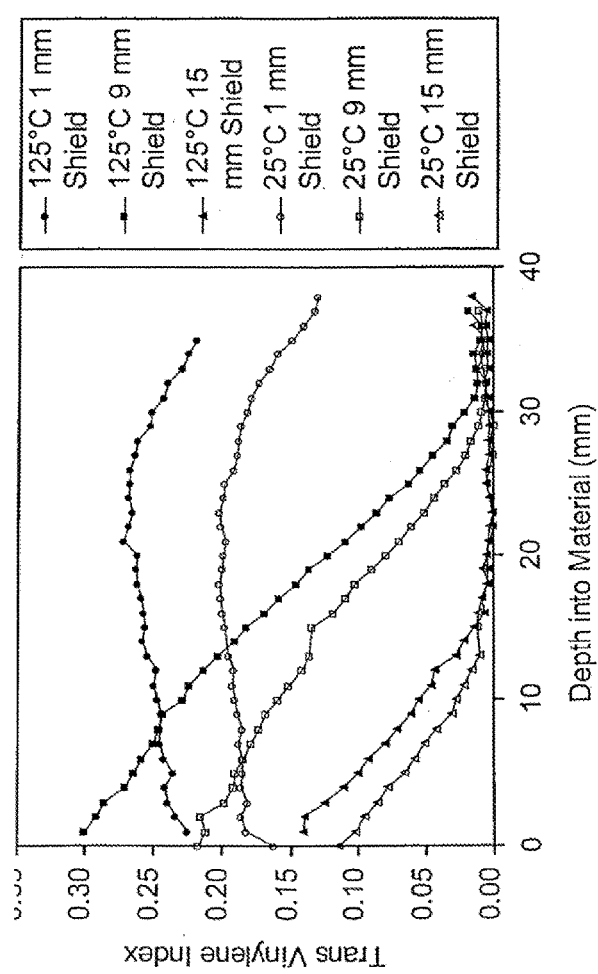
FIG. 3 shows the effects of irradiation at 125° C. compared to irradiation at room temperature in terms of maximum transvinylene index and penetration.

FIG. 3 shows the TVI profiles for UHMWPE that was irradiated at 125° C. and at room temperature (~25° C.) with an aluminum shield of varying thickness. The figures clearly show that the penetration of the effects of e-beam can be controlled by placing an aluminum shield and by varying its thickness. The temperature at which the irradiation is being carried can also be used to change the profile of the beam penetration.

d. Partial Coverage Shielding

Figure 4:
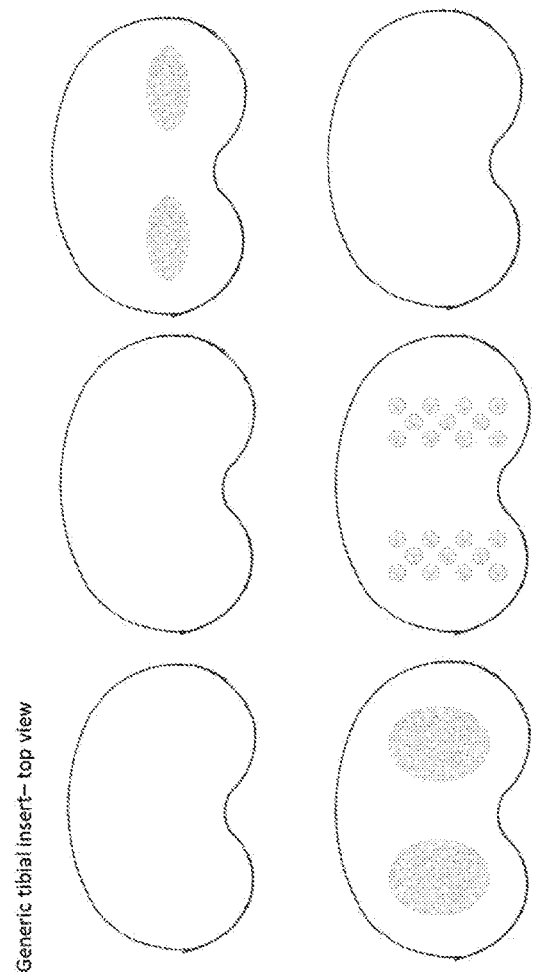
FIG. 4 is a schematic top (radiation-exposed view) of a generic tibial insert with articular regions shielded during irradiation. For example, the shaded regions are not shielded such that they are exposed to the beam during irradiation and are thereafter cross-linked.
Figure 5:
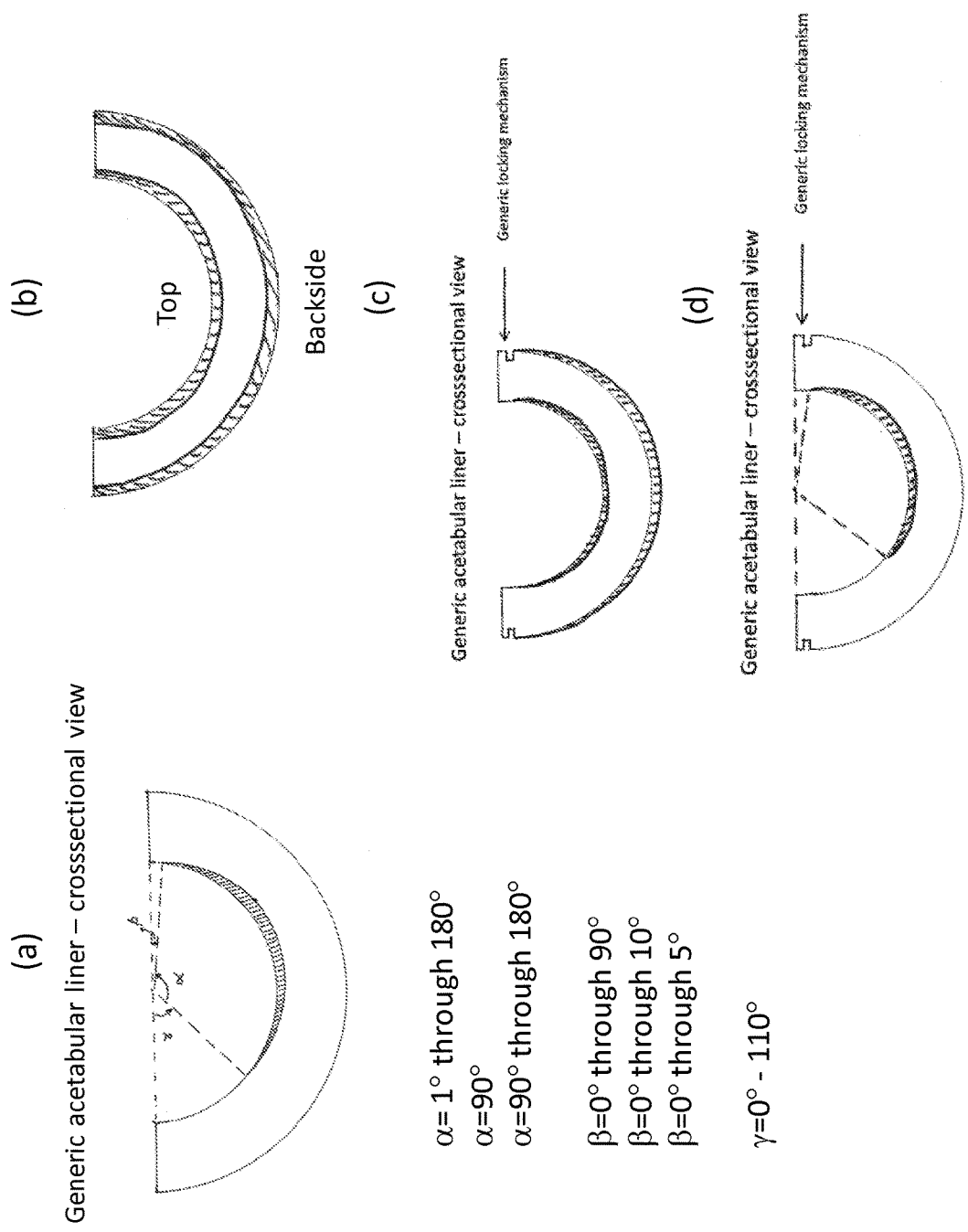
FIG. 5 is a schematic of a generic acetabular liner (cross-sectional view) with surface regions exposed to the beam (a). Shaded areas would be exposed to the low energy beam such that cross-linking takes place in these regions. Elsewhere in the liner or preform, shielding would be used to limit radiation exposure. For example, top and/or backside surfaces of the implant could be shielded such that they are not cross-linked and that locking mechanisms can be machined into these regions (b,c,d). Examples of surface regions (top view) with varying shielding/crosslinking regimes (e).
Figure 5:
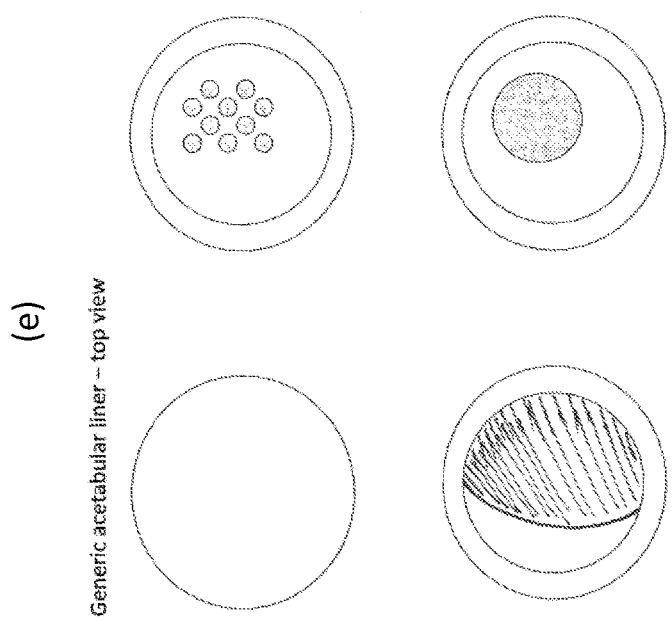
Figure 6:
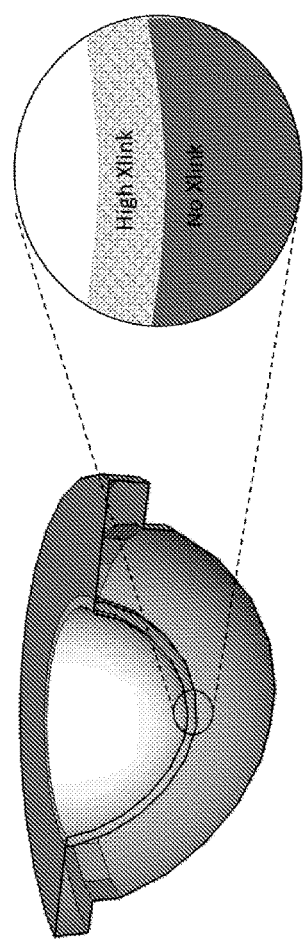
FIG. 6 is a schematic of a hip implant with a highly cross-linked (Xlink) articular surface made by low energy irradiation of a polymer blend with an antioxidant.

FIG. 4 depicts the top (articular surface) view of a generic tibial insert—the tibial insert could be symmetric on the medial and lateral sides or anti-symmetric. FIG. 5 depicts the top (articular surface) view of a generic acetabular liner. The shaded regions depict examples of implant surfaces which are exposed to irradiation and are more cross-linked than the non-shaded regions. The intended purpose of having exposure in the shaded regions is to obtain high levels of crosslinking in these regions after exposure to irradiation (FIG. 6). These types of surfaces can be obtained by low energy irradiation of polymer blends with different antioxidants and different antioxidant concentrations. Shielding can be done at different passes such that there is some cross-linking in different parts of the material. For example, a medical implant preform or medical implant can be irradiated with shielding of some surfaces to 100 kGy in 4 passes, then to 25 kGy in a $5^{th}$ pass such that some parts of the surfaces are more cross-linked then others.

If the surface to be irradiated comprises curvature or curvatures, then the shield could be fabricated or machined to be conforming to the surface intended for irradiation. If partial shielding is desired, then the shield could be machined such that it is conforming to and or covering only parts of the surface(s).

When the irradiation is carried out above the melting point of UHMWPE, the crystallinity decreases significantly and melt-irradiated UHMWPE becomes more transparent. The decrease in the crystallinity is also associated with a decrease in modulus. Therefore, one can use the procedure described here to manufacture different shaped UHMWPE with regions of lower modulus for specific medical applications such as a synthetic glenoid or an intervertebral disc surface.

The shape and cross-section of the shield also plays an important role in determining the properties of the irradiated polymer. Any shape and cross-section shield, or combination of shapes and cross-sections, may be utilized to achieve a desired cross-link depth and pattern.

"Complete" coverage shielding, denoting the use of a shield that covers the entire surface of the polymer being irradiated, is characterized by a cross-linking gradient parallel to the direction of irradiation. That is, due to the shield (including, for example, a portion of the polymer itself), there will be differences in the degree of cross-linking, resulting in a gradient ranging from extensively cross-linked to non-cross-linked, in the plane of the preform that is parallel to the vector that defines the direction of the radiation from the source to the preform.

In other embodiments, other shields may be placed on or over the surface of the polymer such that the depth of penetration of irradiation, as the resulting cross-linking, is affected. In another embodiment of complete coverage shielding, the preform is rotated along an axis passing through the interior of the preform. This embodiment results in a gradient of cross-linking parallel to the vector that defines the direction of the radiation from the source to the preform and in which outer portion of the preform are more extensively cross-linked relative to the inner portion.

"Partial" coverage shielding, denoting the use of a shield that does not cover the entire surface of the polymer being irradiated, may be characterized by a cross-linking gradient perpendicular and/or parallel to direction of irradiation using low energy irradiation. That is, due to the shield, there will be differences in the degree of cross-linking, ranging from extensively cross-linked to non-cross-linked, in the plane of the preform that is perpendicular to the vector that defines the direction of the radiation from the source to the preform and/or there will be differences in the degree of crosslinking, ranging from extensively cross-linked to non-cross-linked, in the plane of the preform that is parallel to the vector that defines the direction of the radiation from the source to the preform due to the energy of the beam. Due to propagation of the electrons in the irradiated preform, a degree of cross-linking may occur under the outer edges of the shield. Thus, where differential shielding has been performed, a gradient of fuller cross-linking to comparatively lesser cross-linking or no crosslinking will be observed in the polymeric material close to the edges of the shield. Thus, cross-linking will be greatest in the unshielded areas, begin to decrease at the interface of the shield and an unshielded (or lesser shielded) edge, and decrease further, or be absent altogether (depending upon the thickness and consistency of the shield), at the inner portions under the shielded area.

Medical implant preforms to be irradiated can be obtained by direct compression molding of layers of polymer blends with antioxidant(s). Alternatively, these compression molded shapes can be further machined to form the articular or backside surfaces or in other parts of the implant for example to machine locking mechanisms. Alternatively, these implants can be machined from a previously consolidated (ram extrusion, compression molding, direct compression molding) UHMWPE/antioxidant blend.

Increasing Uniformity of Cross-Linking

Figure 7:
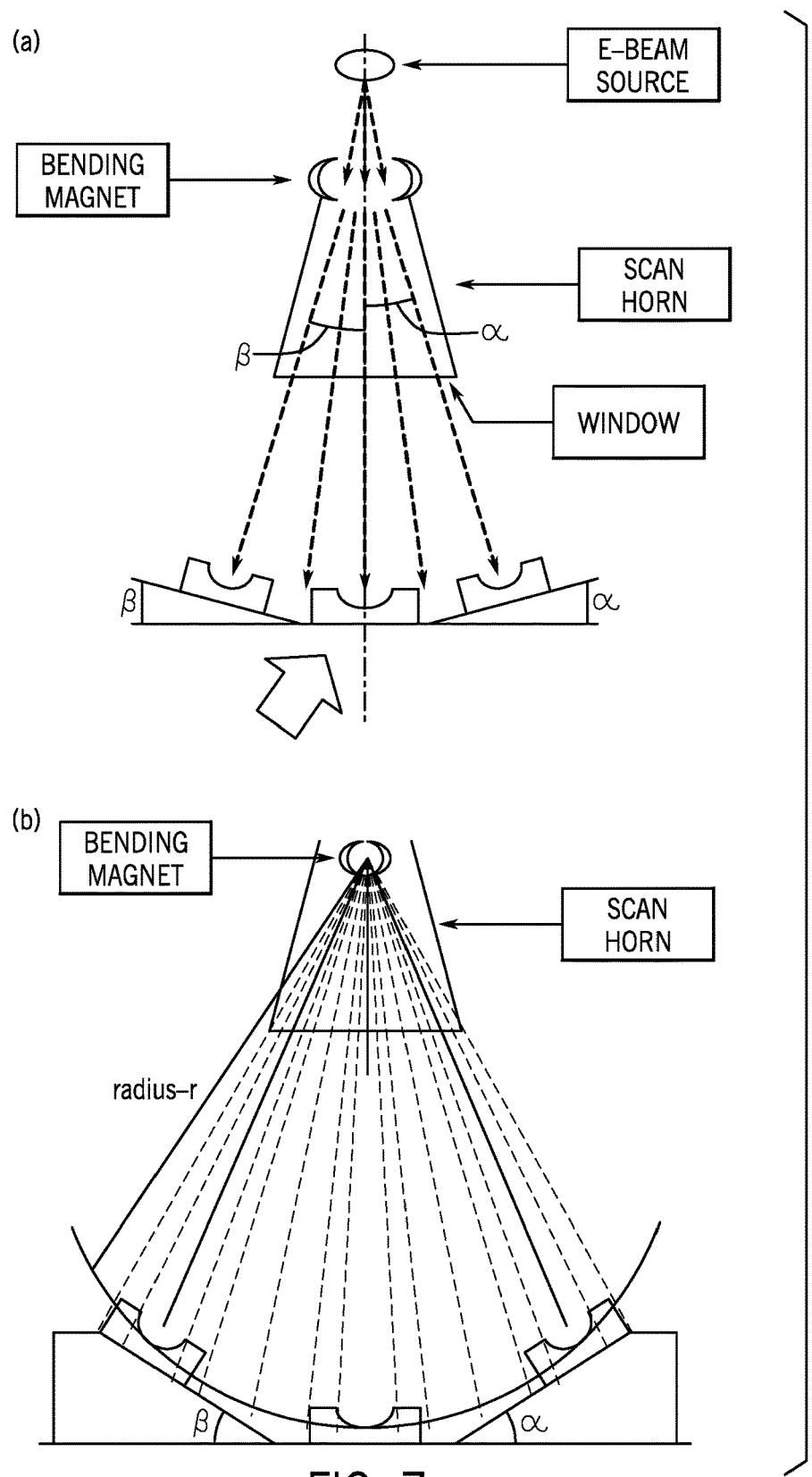
FIG. 7 shows schematic depictions of a vertical electron beam irradiation system. The electrons leave the source, they are guided down to the scan horn through a bending magnet. When they reach the conveyor belt, where the samples are situated, the electrons can be incident at the surface at representative angles, α and β. The figure depicts a method by which the samples are situated at angles, for example, α and β, from the horizontal plane of the conveyor belt such that the incident electrons on the apex of curved surfaces of the medical implant material are normal to the surface. During radiation processing, the conveyor belt moves into the plane of the page.

It is desirable that the incident angle of the electrons on the surface of the polymeric material to be irradiated be normal on the surface and the distance to the surface from the source be equivalent to have a consistent level of cross-linking on the surface and among all the irradiated samples in a batch. FIG. 1 shows a depiction of an electron beam processing unit. The bending magnet guides the electrons from the source into the scan horn from where they travel to the surface of the polymeric material components to be irradiated. FIG. 7 also depicts a design for positioning medical implant preforms containing curved surfaces to be irradiated in a manner to ensure that the incident electrons are normal to the surface at the apex and that they are positioned such that they are the same distance from the electron source. The angles α and β depict deviation of the electrons from the vertical due to the action of the bending magnet. The medical preforms irradiated by the electrons guided along the paths defined by these angles are positioned tilted at a and R, respectively. In this manner, the incident electrons are normal at the apex of each curved surface and they are equidistant from the source.

The angle α or β are representative angles and may be any angle depending on the geometry of the particular beam system. These angles can be from 0 to 90°, more typically between 0 and 50°. They can be any degree from 0 to 90° in 1° intervals or fractions of 1°.

Figure 8:
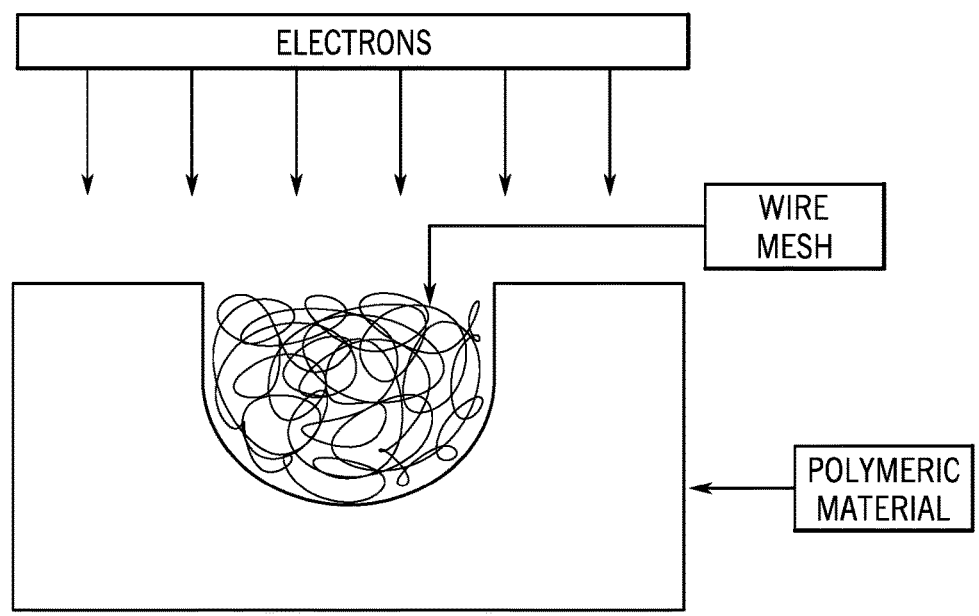
FIG. 8 is a schematic depiction of a secondary material comprising electron scattering fibers in contact with the surfaces of medical implant preform during electron beam irradiation.
Figure 9:
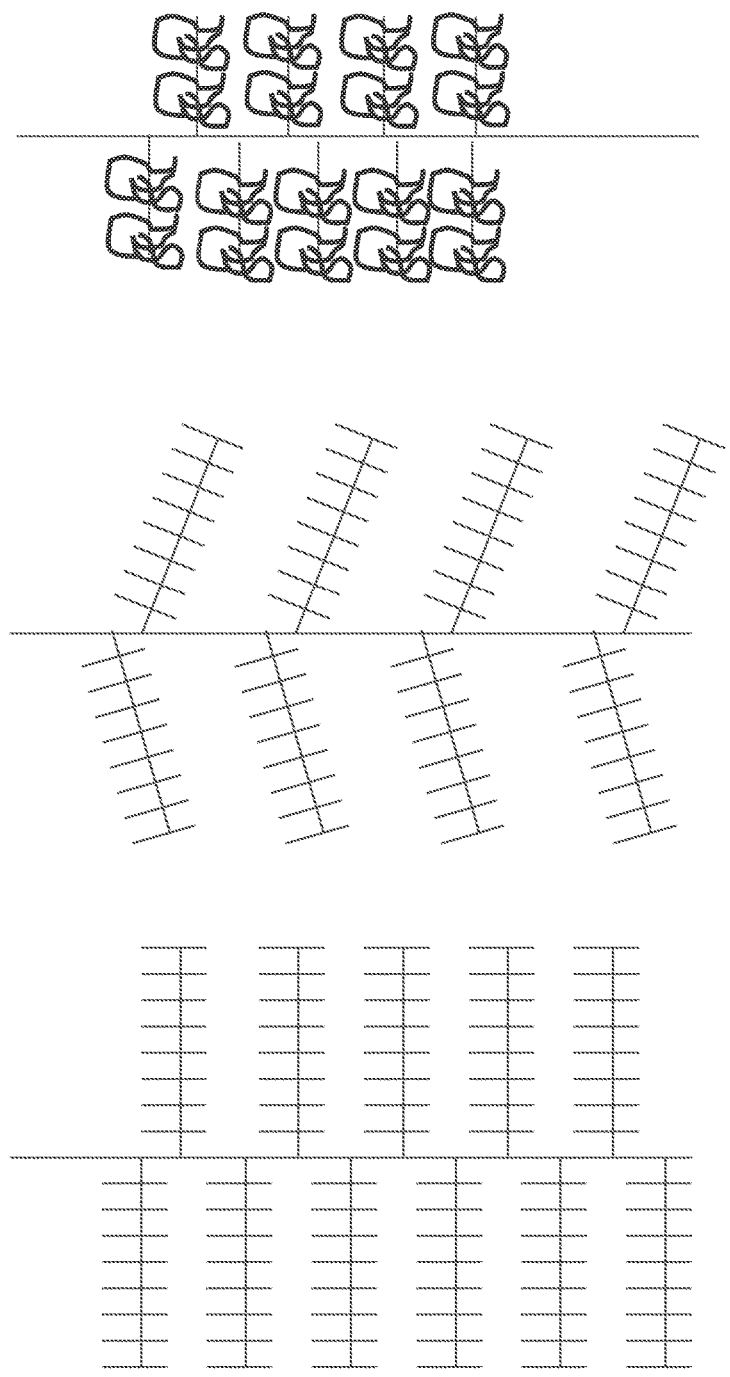
FIG. 9 is a schematic depiction of a secondary material comprising electron scattering fibers arranged in some configurations of brushes.

FIG. 8 depicts a method by which the uniformity of crosslinking of a curved surface of a medical implant preform can be enhanced. Randomly oriented fibers that can scatter the electrons close to the surface of the medical implant preform are placed in contact with or close to the surface of the surfaces to be irradiated during irradiation The fibers can be made of any material, for example metal, plastic-coated metal, metal-coated plastic or solid core metal covered in the same or different metal in a different morphology, preferably metals that can scatter primary electrons and produce secondary electrons. The fibers can be randomly oriented or have one or more preferred orientations, for example they can be woven into wools. The fibers can have a diameter from about 0.001 µm to 1 mm, more preferably about 1 to 50 µm, most preferably about 20 µm. The fiber can be from 1 to 100 µm or more, in 1 µm intervals. The fibers can be in the shape of a brush or brushes connected to a backbone (see FIG. 9). The backbone can be oriented at any direction with respect to the vertical or horizontal depending on which was the beam is oriented.

Figure 10:
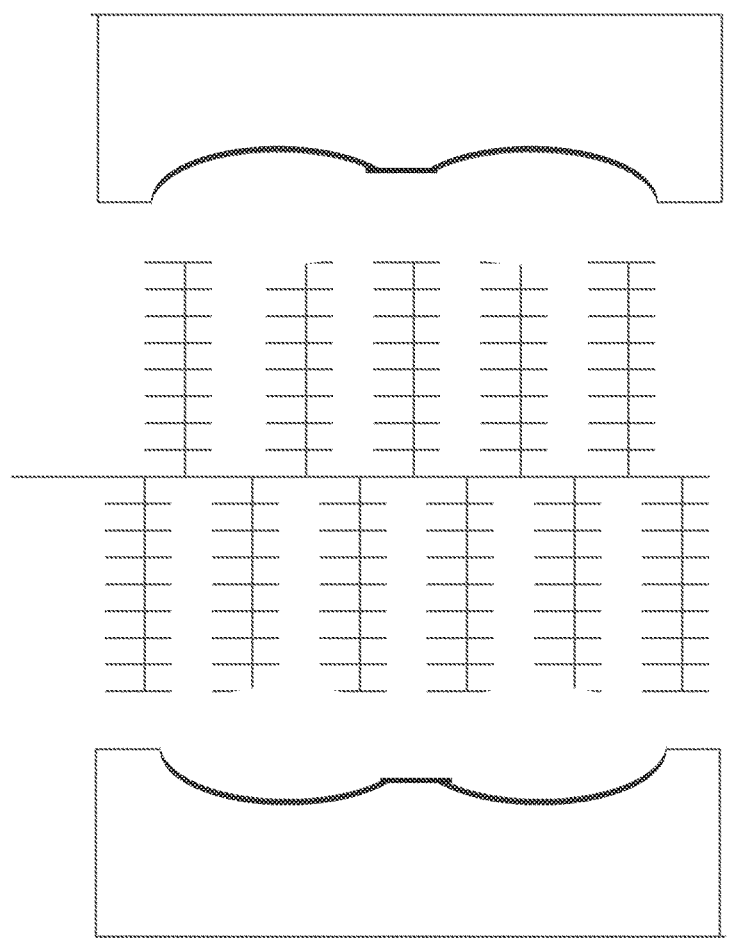
FIG. 10 is a schematic depiction of a secondary material comprising electron scattering fibers close to the surfaces of tibial knee insert preforms during electron beam irradiation. The direction of the electrons could be vertical, horizontal or at any other angle.

The fibers can be effectively individual or agglomerated. The can be arranged in any manner in contact with the surfaces of the medical implant preform, medical implant or polymeric material article to be irradiated (see FIG. 10). They can be situated in direct contact with the surfaces or they can be situated within a close distance of the surfaces. For example, the closest distance from the surface to any part of the scattering fiber geometry can be 0.001 mm to 50 mm, or 1 to 5 mm, or 1 to 50 mm in 1 mm intervals.

The fibers can be made of stainless steel, aluminum, gold, silver, copper, titanium, or any other metal, or mixtures or alloys thereof. The compositions of the mixtures or alloys can be manipulated to change the uniformity of the electron distribution.

Scattering can be by any known mechanism of electron scatter such as inelastic scattering. The energy of the electron beam at the source may need to be increased or decreased to adjust for the scattering component to determine the desired energy to obtain a desired cross-link density at the surface and a desired cross-link density distribution.

In one embodiment, a polymeric material is blended with one or more antioxidants. Then, the blended material is consolidated into stock polymeric material, a medical implant preform or a medical implant. If the consolidated form is stock polymeric material, it can be machined into a medical implant preform or medical implant. Then, the medical implant preform or medical implant is irradiated with the intended surfaces to be irradiated facing the electron beam in contact with or in close proximity to an electron scattering geometry containing fibers using low energy electrons at a temperature close to room temperature, or at a temperature between room temperature and the peak melting point of the polymeric material or above the melting point of the polymeric material.

Modified Morphologies and Low Energy Irradiation

In some embodiments, low energy irradiation of highly crystalline polymeric material can enable the use of highly crystalline, highly cross-linked polymeric material for joint implant articular surfaces. For example, the mechanical strength, as measured by ultimate tensile strength, of high pressure crystallized, highly crystalline UHMWPE is degraded significantly when high dose irradiation is used. This is due to (1) decrease in plastic deformation due to cross-linking (similar to less crystalline UHMWPE) and (2) the deterioration of tie-chain molecules between crystals due to high energy irradiation. Low energy irradiation can enhance the mechanical properties of irradiated, highly crystalline UHMWPE in two ways: (1) by decreasing the energy of the beam, thus decreasing the extent of chain scissioning of the tie-molecules and (2) by limiting cross-linking to the surface, thus decreasing the portion of the material with decreased mechanical strength and maintaining the rest with high mechanical strength.

In some embodiments, a polymeric material is blended with one or more antioxidant(s). The blended polymeric material is consolidated into a medical implant preform or is consolidated into stock, which is then machined into a medical implant preform. The stock or medical implant preform is high pressure crystallized to obtain a highly crystalline stock or medical implant preform. The medical implant preform made from highly crystalline stock is irradiated with its surfaces closest to the intended articular surfaces. Then, the component is contacted with an antioxidant to diffuse more antioxidant on the irradiated surface(s) of the component. Then, the antioxidant-diffused irradiated material is optionally heated to homogenize the antioxidant concentration through the polymeric material. Then, the medical implant preform is machined to form a medical implant. The medical implant is then packaged, and sterilized by gamma sterilization or by gas sterilization such as ethylene oxide or gas plasma sterilization.

In some embodiments, a polymeric material is blended with one or more antioxidants. The blended polymeric material is consolidated into a medical implant preform or is consolidated into stock, which is then machined into a medical implant preform. The stock or medical implant preform is high pressure crystallized to obtain a highly crystalline stock or medical implant preform. Then, the medical implant preform or medical implant is irradiated with the intended surfaces to be irradiated facing the electron beam in contact with or in close proximity to an electron scattering geometry containing fibers using low energy electrons at a temperature close to room temperature, or at a temperature between room temperature and the peak melting point of the polymeric material or above the melting point of the polymeric material.

Melting the surface of a highly crystalline material during irradiation may be advantages such that the amorphous content available for cross-linking is increased. The material can be pre-heated before irradiation to a temperature close to but below the melting temperature and the surface material can be molten during irradiation by the heating imparted by the radiation. In some embodiments, a polymeric material is blended with one or more antioxidant(s). The blended polymeric material is consolidated into a medical implant preform or is consolidated into stock, which is then machined into a medical implant preform. The stock or medical implant preform is high pressure crystallized to obtain a highly crystalline stock or medical implant preform. The medical implant preform made from highly crystalline stock is pre-heated before irradiation and is irradiated with its surfaces closest to the intended articular surfaces such that some or all of the material exposed to irradiation is molten. Then, the component is contacted with an antioxidant to diffuse more antioxidant on the irradiated surface(s) of the component. Then, the antioxidant-diffused irradiated material is optionally heated to homogenize the antioxidant concentration through the polymeric material. Then, the medical implant preform is machined to form a medical implant. The medical implant is then packaged, and sterilized by gamma sterilization or by gas sterilization such as ethylene oxide or gas plasma sterilization.

In some embodiments, a polymeric material is blended with one or more antioxidant(s). The blended polymeric material is consolidated into a medical implant preform or is consolidated into stock under high temperature and pressure, for example 240° C. and 400 MPa. The medical implant preform made from highly crystalline stock is pre-heated before irradiation and is irradiated with its surfaces closest to the intended articular surfaces such that the some or all of the material exposed to irradiation is molten. Then, the component is contacted with an antioxidant to diffuse more antioxidant on the irradiated surface(s) of the component. Then, the antioxidant-diffused irradiated material is optionally heated to homogenize the antioxidant concentration through the polymeric material. Then, the medical implant preform is machined to form a medical implant. The medical implant is then packaged, and sterilized by gamma sterilization or by gas sterilization such as ethylene oxide or gas plasma sterilization.

In some embodiments, low energy irradiation can enable the retention of the toughness of high temperature melted polymeric material. For example, a compression molded UHMWPE puck (10 cm diameter, ~1 cm thickness) melted at 300° C. for 5 hours or 320° C. for 2 hours had higher impact strength than an untreated UHMWPE (140±4 and 139±19 kJ/m$^2$, respectively, compared to 127±7 kJ/m$^2$). When a UHMWPE melted at 300° C. for 5 hours was irradiated uniformly to 150 kGy, the impact strength decreased to 83±3 kJ/m$^2$. Using a linear dependence on thickness, a 10 mm-thick implant with a 2 mm cross-linked surface at these levels would have an impact strength of about 128 kJ/m$^2$, which would be about 50% higher than the uniformly cross-linked, high temperature melted UHMWPE.

In some embodiments, a polymeric material is blended with one or more antioxidant(s). The blended polymeric material is consolidated into a medical implant preform or is consolidated into stock, which is then machined into a medical implant preform. The medical implant preform is high temperature melted. The high temperature melted medical implant preform is irradiated using low energy irradiation with its surfaces closest to the intended articular surfaces. Then, the component is contacted with an antioxidant to diffuse more antioxidant on the irradiated surface(s) of the component. Then, the antioxidant-diffused irradiated material is optionally heated to homogenize the antioxidant concentration through the polymeric material. Then, the medical implant preform is machined to form a medical implant. The medical implant is then packaged, and sterilized by gamma sterilization or by gas sterilization such as ethylene oxide or gas plasma sterilization.

In some embodiments, a polymeric material is blended with one or more antioxidants. The blended polymeric material is consolidated into a medical implant preform or is consolidated into stock, which is then machined into a medical implant preform. The stock or medical implant preform is high temperature melted to obtain a medical implant preform with improved elongation. Then, the medical implant preform or medical implant is irradiated with the intended surfaces to be irradiated facing the electron beam in contact with or in close proximity to an electron scattering geometry containing fibers using low energy electrons at a temperature close to room temperature, or at a temperature between room temperature and the peak melting point of the polymeric material or above the melting point of the polymeric material.

Other Treatments to Enhance the Properties of Low Energy Irradiated Antioxidant-Stabilized Polymeric Material Several post-crosslinking treatments may be utilized to improve the oxidation resistance, wear resistance, or mechanical strength of the polymeric material. For example, high pressure crystallization of UHMWPE leads to the formation of a hexagonal crystalline phase and induces higher crystallinity and higher mechanical strength in uncross-linked and cross-linked UHMWPE, more so in the presence of a plasticizing agent such as vitamin E. High pressure crystallization methods are described in Muratoglu et al. (U.S. Patent Application Publication Nos. 2007/0265369 and 2007/0267030).

To prevent oxidation on the antioxidant-poor region(s), the cross-linked polymeric material, medical implant preform or medical implant can be treated by using one or more of the following methods:

(1) doping with antioxidant(s) through diffusion at an elevated temperature below or above the melting point of the cross-linked polymeric material;

(2) mechanically deforming of the UHMWPE at a temperature between 10° C. and above the melting point of the irradiated polymeric material followed by heating below or above the melting point of the deformed polymeric material;

(3) high pressure crystallization or high pressure annealing of the polymeric material; and (4) further heat treating the polymeric material.

After one or more of these treatments, the free radicals are reduced, stabilized, or practically eliminated everywhere in the article.

It may be desirable that after cross-linking, any heat treatments close to or above the melting temperature of the polymeric material not decrease the crystallinity significantly. A decrease in crystallinity is accompanied by a decrease in mechanical strength, as determined by impact strength, ultimate tensile strength or fatigue strength. However the deleterious effects of melting after irradiation that reduce the crystallinity and hence the strength are minimized when only a thin surface layer of the polymeric material is cross-linked by the use of low energy electron beam.

To maintain the crystallinity of the polymeric material, the heat treatments involved in diffusion of the antioxidant(s) and/or the cross-inking agent(s) and the activation of the crosslinking agent(s) can be performed under pressure to elevate the melting temperature of the polymeric material. In this way, melting during or after cross-linking can be avoided and mechanical properties maintained.

In some embodiments, mechanical annealing of cross-linked polymeric material can be performed. Methods for mechanical annealing of uncross-linked and cross-linked polymeric materials, also in the presence of antioxidants and plasticizing agents are described in Muratoglu et al. (U.S. Patent Application Publication Nos. 2005/0124718, 2004/0156879, 2007/0265369, and 2007/0267030), which are incorporated herein as reference. In another embodiment, invention provides methods to improve oxidative stability of polymers by mechanically deforming the irradiated antioxidant-containing polymers to reduce or eliminate the residual free radicals. Mechanical deformation methods have been described by Muratoglu et al. (see, e.g., U.S. Patent Application Publication Nos. 2004/0156879 and 2005/0124718; and PCT International Application Publication No. WO 2005/074619), which are incorporated herein by reference.

The present invention also describes methods that allow reduction in the concentration of residual free radical in irradiated polymer, in some cases to undetectable levels, without heating the material above its melting point. This method involves subjecting an irradiated sample to a mechanical deformation that is below the melting point of the polymer. The deformation temperature could be as high as about 135° C., for example, for irradiated UHMWPE. The deformation causes motion in the crystalline lattice, which permits recombination of free radicals previously trapped in the lattice through cross-linking with adjacent chains or formation of trans-vinylene unsaturations along the backbone of the same chain. If the deformation is of sufficiently small amplitude, plastic flow can be avoided. The percent crystallinity should not be compromised as a result. Additionally, it is possible to perform the mechanical deformation on machined components without loss in mechanical tolerance. The material resulting from the present invention is a cross-linked polymeric material that has reduced concentration of residuals free radical, and preferably substantially no detectable free radicals, while not substantially compromising the crystallinity and modulus.

The present invention further describes that the deformation can be of large magnitude, for example, a compression ratio of two in a channel die. The deformation can provide enough plastic deformation to mobilize the residual free radicals that are trapped in the crystalline phase. It also can induce orientation in the polymer that can provide anisotropic mechanical properties, which can be useful in implant fabrication. If not desired, the polymer orientation can be removed with an additional step of heating at an increased temperature below or above the melting point.

According to another aspect of the invention, a high strain deformation can be imposed on the irradiated component. In this fashion, free radicals trapped in the crystalline domains likely can react with free radicals in adjacent crystalline planes as the planes pass by each other during the deformation-induced flow. High frequency oscillation, such as ultrasonic frequencies, can be used to cause motion in the crystalline lattice. This deformation can be performed at elevated temperatures that are below the melting point of the polymeric material, and with or without the presence of a sensitizing gas. The energy introduced by the ultrasound yields crystalline plasticity without an increase in overall temperature.

The present invention also provides methods of further heating following free radical elimination below melting point of the polymeric material. According to the invention, elimination of free radicals below the melt is achieved either by the sensitizing gas methods and/or the mechanical deformation methods. Further heating of cross-linked polymer containing reduced or no detectable residual free radicals is done for various reasons, for example:

1. Mechanical deformation, if large in magnitude (for example, a compression ratio of two during channel die deformation), will induce molecular orientation, which may not be desirable for certain applications, for example, acetabular liners. Accordingly, for mechanical deformation:
   a) Thermal treatment below the melting point (for example, less than about 137° C. for UHMWPE) is utilized to reduce the amount of orientation and also to reduce some of the thermal stresses that can persist following the mechanical deformation at an elevated temperature and cooling down. Following heating, it is desirable to cool down the polymer at a slow enough cooling rate (for example, at about 10° C./hour) so as to minimize thermal stresses. If under a given circumstance, annealing below the melting point is not sufficient to achieve reduction in orientation and/or removal of thermal stresses, one can heat the polymeric material to above its melting point.
   b) Thermal treatment above the melting point (for example, more than about 137° C. for UHMWPE) can be utilized to eliminate the crystalline matter and allow the polymeric chains to relax to a low energy, high entropy state. This relaxation leads to the reduction of orientation in the polymer and substantially reduces thermal stresses. Cooling down to room temperature is then carried out at a slow enough cooling rate (for example, at about 10° C./hour) so as to minimize thermal stresses.

2. The contact before, during, and/or after irradiation with a sensitizing environment to yield a polymeric material with no substantial reduction in its crystallinity when compared to the reduction in crystallinity that otherwise occurs following irradiation and subsequent or concurrent melting. The crystallinity of polymeric material contacted with a sensitizing environment and the crystallinity of radiation treated polymeric material is reduced by heating the polymer above the melting point (for example, more than about 137° C. for UHMWPE). Cooling down to room temperature is then carried out at a slow enough cooling rate (for example, at about 10° C./hour) so as to minimize thermal stresses.

As described herein, it is demonstrated that mechanical deformation can eliminate residual free radicals in a radiation cross-linked UHMWPE. The invention also provides that one can first deform UHMWPE to a new shape either at solid- or at molten-state, for example, by compression. According to a process of the invention, mechanical deformation of UHMWPE when conducted at a molten-state, the polymer is crystallized under load to maintain the new deformed shape. Following the deformation step, the deformed UHMWPE sample is irradiated below the melting point to cross-link, which generates residual free radicals. To eliminate these free radicals, the irradiated polymer specimen is heated to a temperature below the melting point of the deformed and irradiated polymeric material (for example, up to about 135° C. for UHMWPE) to allow for the shape memory to partially recover the original shape. Generally, it is expected to recover about 80-90% of the original shape. During this recovery, the crystals undergo motion, which can help the free radical recombination and elimination. The above process is termed as a 'reverse-IBMA'. The reverse-IBMA (reverse-irradiation below the melt and mechanical annealing) technology can be a suitable process in terms of bringing the technology to large-scale production of UHMWPE-based medical devices.

The consolidated polymeric materials according to any of the methods described herein can be irradiated at room temperature or at an elevated temperature below or above the melting point of the polymeric material. In certain embodiments of the present invention any of the method steps disclosed herein, including blending, mixing, consolidating, quenching, irradiating, annealing, mechanically deforming, doping, homogenizing, heating, melting, and packaging of the finished product, such as a medical implant, can be carried out in presence of a sensitizing gas and/or liquid or a mixture thereof, inert gas, air, vacuum, and/or a supercritical fluid.

In certain embodiments, performing any of the methods described herein including high temperature melting, high pressure crystallization, heating, annealing, mechanical deformation, mechanical deformation and annealing, heating under pressure, doping, homogenizing, melting, machining, packaging of the finished product can be carried out before irradiation.

Definitions and Other Embodiments

The term 'low energy irradiation' refers to irradiation which has limited penetration into a polymeric material due to the low energy of the radiation source. For electron beam irradiation, low energy irradiation is defined as electron energies less than 16 MeV, preferably less than 10 MeV, preferably less than 5 MeV, preferably less than 2 MeV such that even without a shield, the penetration of the irradiation into a polymeric material such as UHMWPE is limited to for instance about 8 cm, or preferably 5 cm, or preferably 1 cm, or less. Polymeric materials can be generalized in this manner because most carbon-based polymeric materials have a density near 1 g/cm³.

"Antioxidant" refers to what is known in the art as compound(s) which slow down, inhibit or prevent oxidation in other molecules when present (see, for example, PCT International Application Publication No. WO 01/80778 and U.S. Pat. No. 6,448,315). Alpha- and delta-tocopherol; propyl, octyl, or dodecyl gallates; lactic, citric, ascorbic, tartaric acids, and organic acids, and their salts; orthophosphates, lycopene, tocopherol acetate are generally known form of antioxidants. Antioxidants are also referred as free radical scavengers, include: glutathione, lipoic acid, vitamins such as ascorbic acid (vitamin C), vitamin B, vitamin D, vitamin-E, tocopherols (synthetic or natural, alpha-, gamma-, delta-), acetate vitamin esters, water soluble tocopherol derivatives, tocotrienols, water soluble tocotrienol derivatives; melatonin, carotenoids, including various carotenes, lutein, pycnogenol, glycosides, trehalose, polyphenols and flavonoids, quercetin, lycopene, lutein, selenium, nitric oxide, curcuminoids, 2-hydroxytetronic acid; cannabinoids, synthetic antioxidants such as tertiary butyl hydroquinone, 6-amino-3-pyrodinoles, butylated hydroxyanisole, butylated hydroxytoluene, ethoxyquin, tannins, propyl gallate, other gallates, Aquanox family; Irganox® and Irganox® B families including Irganox® 1010, Irganox® 1076, Irganox® 1330; Irgafos® family including Irgafos® 168; phenolic compounds with different chain lengths, and different number of OH groups; enzymes with antioxidant properties such as superoxide dismutase, herbal or plant extracts with antioxidant properties such as St. John's Wort, green tea extract, grape seed extract, rosemary, oregano extract, mixtures, derivatives, analogues or conjugated forms of these. Antioxidants/free radical scavengers can be primary antioxidants with reactive OH or NH groups such as hindered phenols or secondary aromatic amines, they can be secondary antioxidants such as organophosphorus compounds or thiosynergists, they can be multifunctional antioxidants, hydroxylamines, or carbon centered radical scavengers such as lactones or acrylated bis-phenols. The antioxidants can be selected individually or used in any combination.

Irganox®, as described herein refers to a family of antioxidants manufactured by Ciba Specialty Chemicals. Different antioxidants are given numbers following the Irganox® name, such as Irganox® 1010, Irganox® 1035, Irganox® 1076, Irganox® 1098, etc. Irgafos® refers to a family of processing stabilizers manufactured by Ciba Specialty Chemicals. Irganox® family has been expanded to include blends of different antioxidants with each other and with stabilizers from different families such as the Irgafos family. These have been given different initials after the Irganox® name, for instance, the Irganox® HP family are synergistic combinations of phenolic antioxidants, secondary phosphate stabilizers and the lactone Irganox® HP-136. Similarly, there are Irganox® B (blends), Irganox® L (aminic), Irganox® E (with vitamin E), Irganox® ML, Irganox® MD families. Herein we discuss these antioxidants and stabilizers by their tradenames, but other chemicals with equivalent chemical structure and activity can be used. Addition, these chemicals can be used individually or in mixtures of any composition. Some of the chemical structures and chemical names of the antioxidants in the Irganox® family are listed in Table 1.

TABLE 1

Chemical names and structures of some antioxidants trademarked under the Irganox® name.

| Tradename | Chemical name | Chemical Structure |
|---|---|---|
| Irganox® 1010 | Tetrakis[methylene(3,5-di-tert-butylhydroxyhydrocinnamate)]methane | 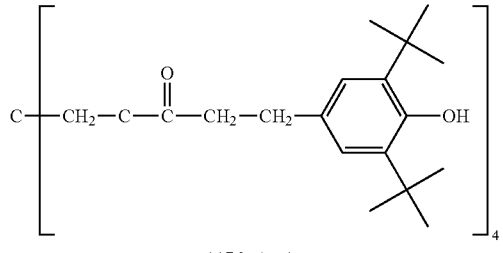 1176 g/mol |
| Irganox® 1035 | Thiodiethylene bis[3-[3,5-di-tert-butyl-4-hydroxyphenyl]propionate] | 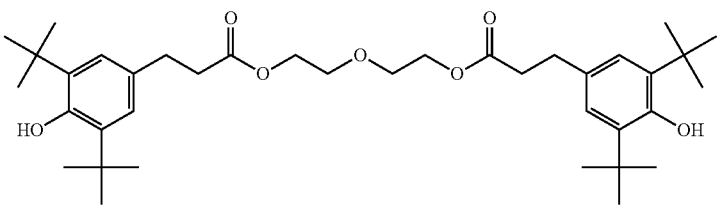 [SMILES: CC(C)(C)c1cc(CCC(=O)OCCOCCOC(=O)CCc2cc(C(C)(C)C)c(O)c(C(C)(C)C)c2)cc(C(C)(C)C)c1O] |
| Irganox® 1076 | Octadecyl 3,5-di-tert-butyl-4-hydroxylhydrocinnamate | 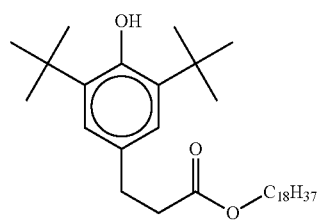 |

TABLE 1-continued

Chemical names and structures of some antioxidants trademarked under the Irganox ® name.

| Tradename | Chemical name | Chemical Structure |
| --- | --- | --- |
| Irganox ® 1098 | N,N'-hexane-1,6-diylbis(3-(3,5-di-tert-butyl-4-hydroxyphenylpropionamide)) | |
| Irganox ® 1135 | Benzenepropanoic acid, 3,5-bis(1,1-dimethyl-ethyl)-4-hydroxy-.C7-C9 branched alkyl esters | 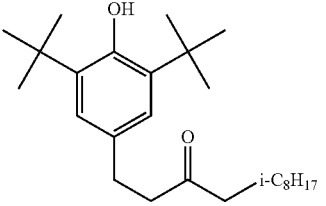<br>390 g/mol |
| Irganox ® 1330 | 1,3,5-tris(3,5-di-tert-butyl-4-hydroxybenzyl)-2,4,6-trimethylbenzene | 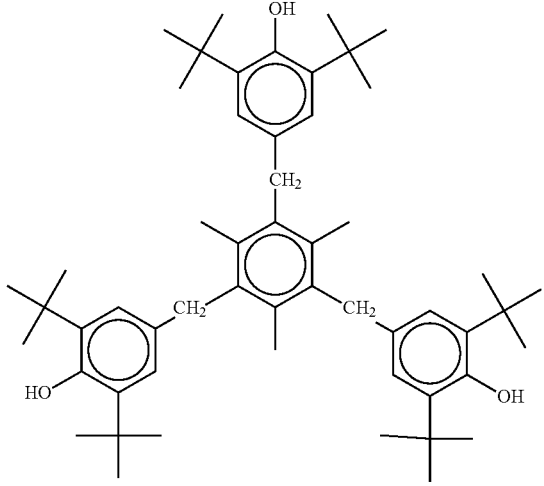 |
| Irganox ® 1520 | | 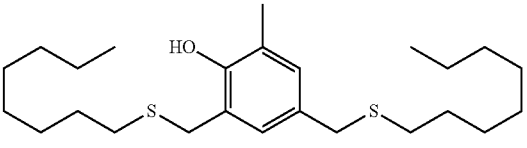 [SMILES: CCCCCCCCSCc1cc(C)c(O)c(CSCCCCCCCC)c1] |
| Irganox ® 1726 | 2,4-bis(dodecylthiomethyl)-6-methylphenol | 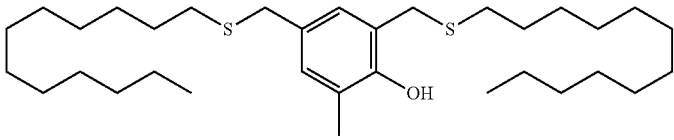 [SMILES: CCCCCCCCCCCCSCc1cc(C)c(O)c(CSCCCCCCCCCCCC)c1] |
| Irganox ® 245 | Triethylene glycol bis(3-tert-butyl-4-hydroxy-5-methylphenyl)propionate | 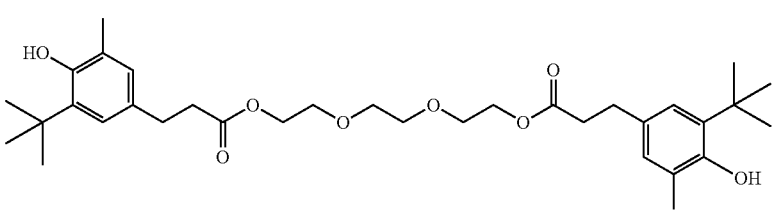 [SMILES: Cc1cc(CCC(=O)OCCOCCOCCOC(=O)CCc2cc(C)c(O)c(C(C)(C)C)c2)cc(C(C)(C)C)c1O] |

TABLE 1-continued

Chemical names and structures of some antioxidants trademarked under the Irganox ® name.

| Tradename | Chemical name | Chemical Structure |
| --- | --- | --- |
| Irganox ® 3052 | 2,2'-methylenebis(4-methyl-6-tert-butylphenol)monoacrylate | 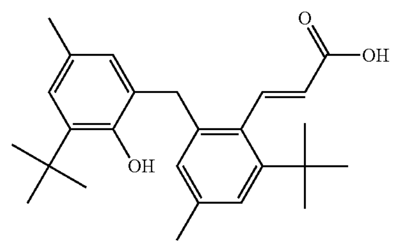 [SMILES: Cc1cc(Cc2cc(C)cc(C(C)(C)C)c2/C=C/C(=O)O)c(O)c(C(C)(C)C)c1] |
| Irganox ® 3114 | 1,3,5-TRis(3,5-di-tert-butyl-4-hydroxybenzyl)-1,3,5-triazine-2,4,6(1H,3H,5H)-trione | 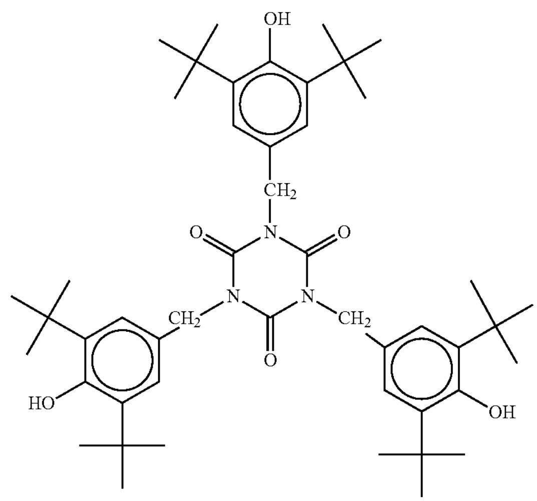 |
| Irganox ® 5057 | Benzenamine,N-phenyl-,reaction products with 2,4,4-trimethylpentene | R, R$_1$ = H, C$_4$H$_9$ or C$_8$H$_{17}$ and other alkyl chains |
| Irganox ® 565 | 2,4-bis(octylthio)-6-(4-hydroxy-3,5-di-tert-butylanilino)-1,3,5-triazine | 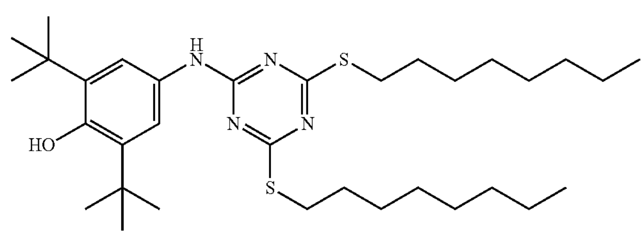 [SMILES: CCCCCCCCSc1nc(Nc2cc(C(C)(C)C)c(O)c(C(C)(C)C)c2)nc(SCCCCCCCC)n1] |
| Irganox ® HP-136 | 5,7-di-t-butyl-3-(3,4 di-methylphenyl)-3H-benzofuran-2-one | 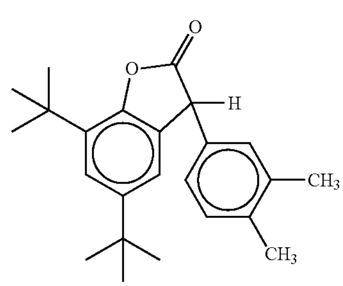 |

TABLE 1-continued

Chemical names and structures of some antioxidants trademarked under the Irganox ® name.

| Tradename | Chemical name | Chemical Structure |
|---|---|---|
| Irgafos ® 168 | Tris(2,4-di-tert-butylphenyl)phospite | 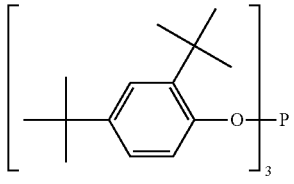<br>646.9 g/mol |

The term "oxidation" refers to the state of polymeric material where reactions with oxygen have taken place such that oxidation products have formed. Generally such a state can be monitored by calculating an 'oxidation index' by obtaining a Fourier transform infrared spectrum for the polymeric material after extraction of non-cross-linked components and analyzing the spectrum to calculate an oxidation index, as the ratio of the areas under the 1740 cm$^{-1}$ carbonyl (limits 1680-1780 cm$^{-1}$) and 1370 cm$^{-1}$ (limits 1330-1390 cm$^{-1}$) methylene stretching absorbance after subtracting the corresponding baselines. Generally speaking an oxidation index of about 0.1 or below is considered baseline levels of oxidation. "Oxidation resistant" refers to a state of polymeric material when there is little or no oxidation or an oxidation index of less than about 0.1 in the material when the material is exposed to oxidizing conditions, for example accelerated aging for 2 weeks at 70° C. in 5 atmospheres of oxygen. "Highly oxidation resistant" refers to a state of polymeric material where there is little or no oxidation or an oxidation index of less than about 0.2 following doping with at least 10 mg of the pro-oxidant squalene diffused into the polymeric material prior to aging and aging for 2 weeks at 70° C. in 5 atmospheres of oxygen.

"Anti-crosslinking agent" is a chemical compound which reduces the resultant cross-link density as a result of cross-linking processes in the polymer such as ionizing radiation exposure when it is blended with the polymer. Anti-cross-linking agents can be antioxidants as well. They can act when they are present in the polymer at any concentration or they may be activated when they are present at a threshold concentration or they may act only when activated by an additional additive.

The term "toughness" of a material refers to its ability to distribute an applied stress such that failure does not occur until there are very high stresses. It is quantified by the area under the stress-strain curve of a material. For example, a higher work-to-failure, which is the area under the engineering stress-strain curve obtained from tensile mechanical testing, is attributed directly to increased toughness. For example, toughness also refers to impact toughness, which is the work-to-failure as measured by impact testing. In the examples, this is demonstrated by IZOD impact testing according to ASTM F648.

The term 'fatigue strength' refers to the resistance of a material to crack formation under cyclic stresses for a prolonged period of time under stress levels lower than its yield strength. It is often characterized by fatigue crack propagation resistance as described, for example in ASTM E647.

The term "substantially sterile" or "sterile" refers to what is known in the art; to a condition of an object that is sufficiently free of biological contaminants and is sufficiently sterile to be medically acceptable, i.e., will not cause an infection or require revision surgery. The object, for example a medical implant, can be sterilized using ionizing radiation or gas sterilization techniques. Gamma sterilization is well known in the art. Electron beam sterilization is also used. Ethylene oxide gas sterilization and gas plasma sterilization are also used. Autoclaving is another method of sterilizing medical implants. Exposure to solvents or supercritical fluids for sufficient to kill infection-causing microorganisms and/or their spores can be a method of sterilizing.

The terms "about" or "approximately" in the context of numerical values and ranges refers to values or ranges that approximate or are close to the recited values or ranges such that the invention can perform as intended, such as utilizing a method parameter (e.g., time, dose, dose rate/level, and temperature), having a desired degree of cross-linking and/or a desired lack of or quenching of free radicals, as is apparent to the skilled person from the teachings contained herein. This is due, at least in part, to the varying properties of polymer compositions. Thus, these terms encompass values beyond those resulting from systematic error. These terms make explicit what is implicit, as known to the person skilled in the art.

"Polymeric materials" or "polymer" include polyethylene, for example, ultra-high molecular weight polyethylene (UHMWPE) refers to linear non-branched chains of ethylene having molecular weights in excess of about 500,000, preferably above about 1,000,000, and more preferably above about 2,000,000. Often the molecular weights can reach about 8,000,000 or more. By initial average molecular weight is meant the average molecular weight of the UHMWPE starting material, prior to any irradiation. See U.S. Pat. No. 5,879,400 and PCT International Application Publication Nos. WO 2001/05337 and WO 97/29793). The term "polyethylene article" or "polymeric article" or "polymer" generally refers to articles comprising any "polymeric material" disclosed herein.

"Polymeric materials" or "polymer" also include hydrogels, such as poly (vinyl alcohol), poly (acrylamide), poly (acrylic acid), poly(ethylene glycol), blends thereof, or inter-penetrating networks thereof, which can absorb water such that water constitutes at least 1 to 10,000% of their original weight, typically 100 wt % of their original weight or 99% or less of their weight after equilibration in water.

"Polymeric material" or "polymer" can be in the form of resin, flakes, powder, consolidated stock, preform, implant, and can contain additives such as antioxidant(s). The "polymeric material" or "polymer" also can be a blend of one or more of different resin, flakes or powder containing different concentrations of an additive such as an antioxidant. The blending of resin, flakes or powder can be achieved by the blending techniques known in the art. The "polymeric material" also can be a consolidated stock of these blends.

"Polymeric material" can be in the form of a consolidated stock that can be machined to form a preform or an implant preform or an implant.

"Polymeric material" can be in the form of a consolidated preform that can be machined to form an implant.

"Polymeric material" can be in the form of a consolidated implant preform that can be machined to form an implant.

"Polymeric material" can be in the form of a direct compression molded implant preform that can be machined to form an implant.

"Polymeric material" can be in the form of a direct compression molded implant preform that can be machined to form an implant.

"Polymeric material" can be in the form of a direct compression molded implant.

What is meant by blend is the combination of two or more constituents to form a mixture thereof. A blend can be formed by the combination of multiple polymers or a combination of additives with one or more types of polymer. For example, an antioxidant/UHMWPE blend may constitute one or more antioxidants mixed with UHMWPE resin powder. The concentration of any of the components or constituents in the blend can be from trace amounts for example 0.0001 wt % to 99.9999 wt %. Typically, an additive will be less than 50% of the blend and the concentration of the polymer or the polymeric material will be more than 50%.

Blending generally refers to mixing of a polymeric material in its pre-consolidated form with an additive. If both constituents are solid, blending can be done by using other component(s) such as a liquid or solvent to mediate the mixing of the two components, after which the liquid is removed by evaporation. If the additive itself is liquid, for example α-tocopherol at room temperature, then the polymeric material can be mixed with large quantities of the liquid additive to obtain a high concentration blend. This high concentration blend can be diluted down to desired blend concentrations with the addition of lower concentration blends or virgin polymeric material without the additive to obtain the desired concentration blend. The high concentration blend and the low concentration blend (or virgin polymeric material without the additive) can be blended together by simple mixing and shaking. This technique of mixing high and low concentration blends also results in improved uniformity of the distribution of the additive in the polymeric material. In the case where an additive is also an antioxidant, for example vitamin E, or α-tocopherol, then blended polymeric material is also antioxidant-doped. Polymeric material, as used herein, also applies to blends of a polyolefin and a cross-linking agent, for example a blend of UHMWPE resin powder blended with peroxide(s) and consolidated. Polymeric material, as used herein, also applies to blends of antioxidant(s), polyolefin(s) and crosslinking agent(s).

"Blending" generally refers to mixing of a polyolefin in its pre-consolidated form with an additive. If both constituents are solid, blending can be done dry or by using a third component such as a liquid to mediate the mixing of the two components, after which the liquid is removed by evaporating ('solvent blending'). If the additive is liquid, for example α-tocopherol, then the solid can be mixed with large quantities of liquid, then diluted down to desired concentrations with the solid polymer to obtain uniformity in the blend. In the case where an additive is also an antioxidant, for example vitamin E, or α-tocopherol, then blended polymeric material is also antioxidant-doped. Polymeric material, as used herein, also applies to blends of a polyolefin and a plasticizing agent, for example a blend of UHMWPE resin powder blended with α-tocopherol and consolidated. Polymeric material, as used herein, also applies to blends of an additive, a polyolefin and a plasticizing agent, for example UHMWPE soaked in α-tocopherol.

The additive in the blend, for example, vitamin E can be from 0.001 wt % to 99 wt %, more preferably from 0.05 wt % to 3 wt % or more, more preferably from 0. Wt % to 1 wt % in 0.1 wt % intervals.

In one embodiment UHMWPE flakes are blended with α-tocopherol; preferably the UHMWPE/α-tocopherol blend is heated to diffuse the α-tocopherol into the flakes. The UHMWPE/α-tocopherol blend is further blended with virgin UHMWPE flakes to obtain a blend of UHMWPE flakes where some flakes are poor in α-tocopherol and others are rich in α-tocopherol. This blend is then consolidated and irradiated. During irradiation the α-tocopherol poor regions are more highly cross-linked than the α-tocopherol poor regions. Following irradiation the blend is homogenized to diffuse α-tocopherol from the α-tocopherol rich to α-tocopherol poor regions and achieve oxidative stability throughout the polymer.

The products and processes of this invention also apply to various types of polymeric materials, for example, any polypropylene, any polyamide, any polyether ketone, or any polyolefin, including high-density-polyethylene, low-density-polyethylene, linear-low-density-polyethylene, ultra-high molecular weight polyethylene (UHMWPE), copolymers or mixtures thereof. The products and processes of this invention also apply to various types of hydrogels, for example, poly(vinyl alcohol), poly(ethylene glycol), poly(ethylene oxide), poly(acrylic acid), poly(methacrylic acid), poly(acrylamide), copolymers or mixtures thereof, or copolymers or mixtures of these with any polyolefin. Polymeric materials, as used herein, also applies to polyethylene of various forms, for example, resin, powder, flakes, particles, powder, or a mixture thereof, or a consolidated form derived from any of the above. Polymeric materials, as used herein, also applies to hydrogels of various forms, for example, film, extrudate, flakes, particles, powder, or a mixture thereof, or a consolidated form derived from any of the above.

Blending of additives in the polymeric material resin can be done by:
1. Dissolving an antioxidant/anti-crosslinking agent in a solvent or a mixture of solvents,
2. Mixing the polymer resin with the antioxidant/anti-crosslinking agent solution,
3. Drying the solvent by evaporation, optionally using elevated temperature or vacuum.

Solvents can be chosen from organic solvents such as acetic acid, acetone, acetonitrile, benzene, butanols, butanone, carbon tetrachloride, chlorobenzene, chloroform, cyclohexane, 1,2-dicholoethane, diethyl ether, diethylene glycol, diethylene glycol diethyl ether, 1,2-dimethoxyethane, dimethyl ether, dimethylformamide, dimethyl sulfoxide, dioxane, ethanol, ethyl acetate, ethylene glycol, glycerin, heptane, hexane, methanol, pentane, propanols, pyridine, tetrahydrofuran, toluene, xylene or they can be aqueous solvents. Aqueous solvents can be pure water or solution of other compounds such as acids, salts, or bases in water. They can be aqueous solutions of surfactants (generally amphiphilic compounds) such as fatty acids. They can also be inorganic non-aqueous solvents such as liquid alumina. Solvent can also be a supercritical fluid such as supercritical carbon dioxide.

The solvent is typically selected depending on the solubility of the antioxidants/anti-crosslinking agents desired to be blended into the polymer. The polymer resin can optionally dissolve in the same solvent. Different antioxidants/anti-crosslinking agents can be dissolved in different solvents and mixed together before mixing in the polymer or can be separately mixed with the polymer powder. In each case more than one solvent can be used. Dissolution of the antioxidants/anti-crosslinking agents can be enhanced or enabled by raising the temperature or pressure or raising the temperature and pressure such that the solvent is in the supercritical state.

The term "additive" refers to any material that can be added to a base polymer in less than 50 v/v %. This material can be organic or inorganic material with a molecular weight less than that of the base polymer. An additive can impart different properties to the polymeric material, for example, it can be a plasticizing agent, a nucleating agent, or an antioxidant.

"Cross-linking Polymeric Materials" refers to polymeric materials, for example, UHMWPE can be cross-linked by a variety of approaches, including those employing cross-linking chemicals (such as peroxides and/or silane) and/or irradiation. Preferred approaches for cross-linking employ irradiation. Cross-linked UHMWPE also can be obtained through cold irradiation, warm irradiation, or melt irradiation according to the teachings of U.S. Pat. Nos. 5,879,400 and 6,641,617, and PCT International Application Publication No. WO 97/29793.

Radiation cross-linking and thermal treatment methods are further defined as follows:

(i) Irradiation in the Molten State (IMS):

Melt-irradiation, or irradiation in the molten state ("IMS"), is described in detail in U.S. Pat. No. 5,879,400. In the IMS process, the polymer to be irradiated is heated to at or above its melting point. Then, the polymer is irradiated. Following irradiation, the polymer is cooled.

Prior to irradiation, the polymer is heated to at or above its melting temperature and maintained at this temperature for a time sufficient to allow the polymer chains to achieve an entangled state. A sufficient time period may range, for example, from about 5 minutes to about 3 hours. For UHMWPE, the polymer may be heated to a temperature between about 145° C. and about 230° C., preferably about 150° C. to about 200° C.

The temperature of melt-irradiation for a given polymer depends on the DSC (measured at a heating rate of 10° C./min during the first heating cycle) peak melting temperature ("PMT") for that polymer. In general, the irradiation temperature in the IMS process is about 2° C. higher than the PMT, more preferably between about 2° C. and about 20° C. higher than the PMT, and most preferably between about 5° C. and about 10° C. higher than the PMT.

The total dose of irradiation also may be selected as a parameter in controlling the properties of the irradiated polymer. In particular, the dose of irradiation can be varied to control the degree of cross-linking and crystallinity in the irradiated polymer. The total dose may range from about 0.1 Mrad to as high as the irradiation level where the changes in the polymer characteristics induced by the irradiation reach a saturation point. For instance the high end of the dose range could be 20 Mrad for the melt-irradiation of UHMWPE, above which dose level the crosslink density and crystallinity are not appreciably affected with any additional dose. The preferred dose level depends on the desired properties that will be achieved following irradiation. Additionally, the level of crystallinity in polyethylene is a strong function of radiation dose level. See Dijkstra et al., Polymer 30: 866-73 (1989). For instance with IMS irradiation, a dose level of about 20 Mrad would decrease the crystallinity level of UHMWPE from about 55% to about 30%. This decrease in crystallinity may be desirable in that it also leads to a decrease in the elastic modulus of the polymer and consequently a decrease in the contact stress when a medical prosthesis made out of the IMS-treated UHMWPE gets in contact with another surface during in vivo use. Lower contact stresses are preferred to avoid failure of the polymer through, for instance, subsurface cracking, delamination, fatigue, etc. The increase in the crosslink density is also desirable in that it leads to an increase in the wear resistance of the polymer, which in turn reduces the wear of the medical prostheses made out of the crosslinked polymer and substantially reduces the amount of wear debris formed in vivo during articulation against a counterface. In general, the melt-irradiation and subsequent cooling will lead to a decrease in the crystallinity of the irradiated polymer.

(ii) Warm irradiation is described in detail in WO 97/29793. In the warm irradiation process, a polymer is provided at a temperature above room temperature and below the melting temperature of the polymer. Then, the polymer is irradiated. In one embodiment of warm irradiation, which has been termed "warm irradiation adiabatic melting" or "WIAM" the polymer may be irradiated at a high enough total dose and/or a high enough dose rate to generate enough heat in the polymer to result in at least a partial melting of the crystals of the polymer.

The adiabatic temperature rise depends on the dose level, level of insulation, and/or dose rate. Exemplary ranges of acceptable total dosages are disclosed in greater detail in PCT International Application Publication No. WO 97/29793. In the embodiments below, UHMWPE is used as the starting polymer. In one embodiment, the total dose is about 0.5 MRad to about 1,000 Mrad. In another embodiment, the total dose is about 1 MRad to about 100 MRad. In yet another embodiment, the total dose is about 4 MRad to about 30 MRad. In still other embodiments, the total dose is about 20 MRad or about 15 MRad.

The polymer may be provided at any temperature below its melting point and above room temperature. The temperature selection depends on the specific heat and the enthalpy of melting of the polymer and the total dose level that will be used. The equation provided in International Application WO 97/29793 may be used to calculate the preferred temperature range with the criterion that the final temperature of polymer maybe below or above the melting point. Preheating of the polymer to the desired temperature may be done in an inert or non-inert environment. Exemplary ranges of acceptable total dosages are disclosed in greater detail in International Application WO 97/29793. In one embodiment, the UHMWPE is preheated to about 20° C. to about 135° C. In one embodiment of WIAM, the UHMWPE is preheated to about 100° C. to just below the melting temperature of the polymer. In another embodiment of WIAM, the UHMWPE is preheated to a temperature of about 100° C. to about 135° C. In yet other embodiments of WIAM, the polymer is preheated to about 120° C. or about 130° C.

In general terms, the pre-irradiation heating temperature of the polymer can be adjusted based on the peak melting temperature (PMT) measure on the DSC at a heating rate of 10° C./min during the first heat. In one embodiment the polymer is heated to about 20° C. to about PMT. In another embodiment, the polymer is preheated to about 40° C., 50° C., 60° C., 70° C., 80° C. or 90° C. In another embodiment, the polymer is heated to about 100° C. In another embodiment, the polymer is preheated to about 30° C. below PMT and 2° C. below PMT. In another embodiment, the polymer is preheated to about 12° C. below PMT.

In the 'warm irradiation and adiabatic melting (WIAM)' embodiment of warm irradiation (WIR), the temperature of the polymer following irradiation is at or above the melting temperature of the polymer. Exemplary ranges of acceptable temperatures following irradiation are disclosed in greater detail in International Application WO 97/29793. In one embodiment, the temperature following irradiation is about room temperature to PMT, or about 40° C. to PMT, or about 100° C. to PMT, or about 110° C. to PMT, or about 120° C. to PMT, or about PMT to about 200° C. In another embodiment, the temperature following irradiation is about 145° C. to about 190° C. In yet another embodiment, the temperature following irradiation is about 146° C. to about 190° C. In still another embodiment, the temperature following irradiation is about 150° C.

The dose rate of irradiation also may be varied to achieve a desired result. The dose rate is a prominent variable in the warm irradiation process. In the case of warm irradiation of UHMWPE, higher dose rates would provide the least amount of reduction in toughness and elongation at break. The preferred dose rate of irradiation would be to administer the total desired dose level in one pass under the electron-beam. One can also deliver the total dose level with multiple passes under the beam, delivering a (equal or unequal) portion of the total dose at each time. This would lead to a lower effective dose rate.

In some embodiments, double-sided irradiation may be used to achieve desired penetration depth and dose profiles in the polymeric material.

Ranges of acceptable dose rates are exemplified in greater detail in PCT International Application Publication No. WO 97/29793. In general, the dose rates will vary between 0.5 Mrad/pass and 50 Mrad/pass. The upper limit of the dose rate depends on the resistance of the polymer to cavitation/cracking induced by the irradiation.

Depending on the polymer or polymer alloy used, and whether the polymer was irradiated below its melting point, there may be residual free radicals left in the material following the irradiation process. A polymer irradiated below its melting point with ionizing radiation contains cross-links as well as long-lived trapped free radicals. Some of the free radicals generated during irradiation become trapped at crystalline lamellae surfaces (see Kashiwabara, H. S. Shimada, and Y. Hori, "Free Radicals and Crosslinking in Irradiated Polyethylene", *Radiat. Phys. Chem.*, 1991, 37(1): p. 43-46); leading to oxidation-induced instabilities in the long-term (see Jahan, M. S. and C. Wang, "Combined Chemical and Mechanical Effects on Free radicals in UHM-WPE Joints During Implantation", *Journal of Biomedical Materials Research*, 1991, 25: p. 1005-1017; and Sutula, L. C., et al., "Impact of gamma sterilization on clinical performance of polyethylene in the hip", *Clinical Orthopedic Related Research*, 1995, 3129: p. 1681-1689). The elimination of these residual, trapped free radicals through melt annealing is, therefore, desirable in precluding long-term oxidative instability of the polymer (see Jahan M. S. and C. Wang, "Combined chemical and mechanical effects on free radicals in UHMWPE joints during implantation", *Journal of Biomedical Materials Research*, 1991, 25: p. 1005-1017; and Sutula, L. C., et al., "Impact of gamma sterilization on clinical performance of polyethylene in the hip", *Clinical Orthopedic Related Research*, 1995, 319: p. 28-4).

If there are residual free radicals remaining in the material, these may be reduced to substantially undetectable levels, as measured by electron spin resonance or other tests, through annealing of the polymer above the melting point of the polymeric system used. The melt annealing allows the residual free radicals to recombine with each other. If for a given system the preform does not have substantially any detectable residual free radicals following irradiation, then a melt annealing step may be omitted. Also, if for a given system, the concentration of the residual free radicals is low enough to not lead to degradation of device performance, the melt annealing step may be omitted. In some of the lower molecular weight and lower density polyethylenes, the residual free radicals may recombine with each other even at room temperature over short periods of time, for example, few hours to few days, to few months. In such cases, the subsequent melt-annealing may be omitted if the increased crystallinity and modulus resulting from the irradiation is preferred. Otherwise, the subsequent melt-annealing may be carried out to decrease the crystallinity and modulus. In the case where melt annealing is omitted, the irradiated preform can be directly machined into the final medical device. The subsequent melt-annealing may also also be omitted if the polymer contains enough antioxidant to prevent oxidation in the long-term.

The reduction of free radicals to the point where there are substantially no detectable free radicals can be achieved by heating the polymer to above the melting point. The heating provides the molecules with sufficient mobility so as to eliminate the constraints derived from the crystals of the polymer, thereby allowing essentially all of the residual free radicals to recombine. Preferably, the polymer is heated to a temperature between the peak melting temperature (PMT) and degradation temperature ($T_d$) of the polymer, more preferably between about 3° C. above PMT and $T_d$, more preferably between about 10° C. above PMT and 50° C. above PMT, more preferably between about 10° C. and 12° C. above PMT and most preferably about 15° C. above PMT.

During melt annealing of UHMWPE, the polymer is heated to a temperature of about 137° C. to about 300° C., more preferably about 140° C. to about 300° C., more preferably yet about 140° C. to about 190° C., more preferably yet about 145° C. to about 300° C., more preferably yet about 145° C. to about 190° C., more preferably yet about 146° C. to about 190° C., and most preferably about 150° C. Preferably, the temperature in the heating step is maintained for about 0.5 minutes to about 24 hours, more preferably about 1 hour to about 3 hours, and most preferably about 2 hours. The heating can be carried out, for example, in air, in an inert gas, e.g., nitrogen, argon or helium, in a sensitizing atmosphere, for example, acetylene, or in a vacuum. It is preferred that for the longer heating times, that the heating be carried out in an inert gas or under vacuum to avoid in-depth oxidation.

In certain embodiments, there may be a tolerable level of residual free radicals in which case, the post-irradiation annealing can also be carried out below the melting point of the polymer.

During below the melt annealing of UHMWPE, the polymer is heated to a temperature of about 70° C. to about 300° C., more preferably about 100° C. to about 135° C., more preferably yet about 120° C. to about 130° C., most preferably about 125° C. In cases where the temperature is above the melting temperature of the polymeric material at ambient pressure, the pressure may be increased to elevate the melting temperature and maintain the polymeric material below the melting temperature. Preferably, the temperature in the heating step is maintained for about 0.5 minutes to about 24 hours, more preferably about 1 hour to about 3 hours, and most preferably about 2 hours. The heating can be carried out, for example, in air, in an inert gas, e.g., nitrogen, argon or helium, in a sensitizing atmosphere, for example, acetylene, or in a vacuum. It is preferred that for the longer heating times, that the heating be carried out in an inert gas or under vacuum to avoid in-depth oxidation.

(v) Sequential Irradiation:

The polymer is irradiated in a sequential manner. With e-beam the irradiation is carried out with multiple passes under the beam and with gamma radiation the irradiation is carried out in multiple passes through the gamma source. Optionally, the polymer is thermally treated in between each or some of the irradiation passes. The thermal treatment can be annealing below the melting point, at the melting point or above the melting point of the polymer of the polymer. The irradiation at any of the steps can be warm irradiation, cold irradiation, or melt irradiation, as described above. For example the polymer is irradiated with 30 kGy at each step of the crosslinking and it is first heated to about 120° C. and then annealed at about 120° C. for about 5 hours after each irradiation cycle.

"Consolidated polymeric material" refers to a solid, consolidated bar stock, solid material machined from stock, or semi-solid form of polymeric material derived from any forms as described herein, for example, resin, powder, flakes, particles, or a mixture thereof, that can be consolidated. The consolidated polymeric material also can be in the form of a slab, block, solid bar stock, machined component, film, tube, balloon, preform, implant, finished medical device or unfinished device.

What is meant by "virgin" is a material with no additives. For instance virgin polymeric material is a polymeric material with no additives such as antioxidants. In any of the embodiments, virgin polymeric material can be used where a polymeric material blend is described.

By "crystallinity" is meant the fraction of the polymer that is crystalline. The crystallinity is calculated by knowing the weight of the sample (weight in grams), the heat absorbed by the sample in melting (E, in J/g) and the heat of melting of polyethylene crystals ($\Delta H=291$ J/g), and using the following equation according to ASTM F2625 and the like or their successors:

% Crystallinity=$E/w \cdot \Delta H$

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but not limited to, vegetable parchments, multi-layer polyethylene, Nylon 6, poly-ethylene terephthalate (PET), and polyvinyl chloride-vinyl acetate copolymer films, polypropylene, polystyrene, and ethylene-vinyl acetate (EVA) copolymers.

The term "interface" in this invention is defined as the niche in medical devices formed when an implant is in a configuration where a component is in contact with another piece (such as a metallic or a non-metallic component), which forms an interface between the polymer and the metal or another polymeric material. For example, interfaces of polymer-polymer or polymer-metal are in medical prosthesis, such as orthopedic joints and bone replacement parts, for example, hip, knee, elbow or ankle replacements.

Medical implants containing factory-assembled pieces that are in close contact with the polyethylene form interfaces. In most cases, the interfaces are not readily accessible to ethylene oxide gas or the gas plasma during a gas sterilization process.

Crosslinking agent: is a compound which can cause cross-linking in polymeric materials. Most often, cross-linking of the polymer follows a trigger which initiates the cross-linking process. For example, in the case of peroxides, heating to a temperature where the peroxide decomposes into free radicals, which are then transferred onto the polymer and initiate recombination reactions causing cross-linking is required. In other cases, other stimuli may be used to trigger the reaction such as the application of ultraviolet light, heat, pressure or vacuum, contact with a particular solvent or irradiation or combinations thereof. In this invention the cross-linking agents used are those that are commercially available and may contain impurities. In some embodiments the cross-linking agents may be 100% pure or less. In some embodiments the cross-linking agents are 80%, 85%, 90%, 91%, 92%, 93%, 94%, 95%, 96%, 97%, 98%, and 99% pure.

The definition here differs somewhat from what is known in the art. Typically, a crosslinking agent is defined as a compound which can chemically attach to two or more points on the polymeric material, creating a linkage between the same or different polymer chains. We are using a more general definition where the crosslinking agent is a compound that initiates the processes that lead to the crosslinking of the polymeric material and the compound may or may not itself chemically attach to the polymer. For instance the cross-linking agent may have a free radical, which may abstract a hydrogen from the polymeric material, creating a free radical on the polymeric material; subsequently to such free radicals on the polymeric material can react with each other to form a cross-linked without chemically attaching the cross-linking agent to the polymeric material. In some embodiments, the unreacted cross-linking agent and/or the byproducts of the cross-linking agent are partially or fully extracted from the polymeric material after cross-linking. This extraction among other methods can include solvent extraction, emulsified solvent extraction, heat, and/or vacuum.

Doping: Doping refers to a process well known in the art (see, for example, U.S. Pat. Nos. 6,448,315 and 5,827,904). In this connection, doping generally refers to contacting a polymeric material with a component or the solution/emulsion of a component under certain conditions, as set forth herein, for example, doping UHMWPE with an antioxidant under supercritical conditions. "Doping" also refers to introducing additive(s) into the base polymeric material in quantities less than 50 v/v %. A polymeric material treated in such a way for example to incorporate an antioxidant is termed as an "antioxidant-doped" polymeric material. The polymeric material can be 'doped' by other additives as well, such as a crosslinking agent, in which case the polymeric material treated in such a way may be termed as 'crosslinking agent-doped'. Alternatively, if the polymeric material is doped by one or more peroxides, it may be termed 'peroxide-doped'.

Doping may also be done by diffusing an additive into the polymeric material by immersing the polymeric material by contacting the polymeric material with the additive in the solid state, or with a bath of the additive in the liquid state, or with a mixture of the additive in one or more solvents in solution, emulsion, suspension, slurry, aerosol form or in a gas or in a supercritical fluid. The doping process by diffusion can involve contacting a polymeric material, medical implant or device with an additive, such as vitamin E, for about an hour up to several days, preferably for about one hour to 24 hours, more preferably for one hour to 16 hours. The environment for the diffusion of the additive (bath, solution, emulsion, paste, slurry and the like) can be heated to room temperature or up to about 200° C. and the doping can be carried out at room temperature or up to about 200° C. Preferably, the antioxidant can be heated to 100° C. and the doping is carried out at 100° C. A polymeric material incorporated with an additive by diffusion in such a way is termed an 'additive-diffused' polymeric material. For example, a polymeric material immersed in a bath of anti-oxidant(s) for enough time to dope at least some parts of the polymeric material with the antioxidant(s), is termed an 'antioxidant-diffused' polymeric material. The polymeric material can be 'diffused' by other additives as well, such as a crosslinking agent, in which case the polymeric material treated in such a way may be termed as 'crosslinking agent-diffused'.

To increase the depth of diffusion of the antioxidant, the material can be doped for longer durations, at higher temperatures, at higher pressures, and/or in presence of a supercritical fluid.

The doped polymeric material can be annealed by heating below or above the melting point of the polymeric material subsequent to doping. The annealing is preferably for about an hour up to several days, more preferably for about one hour to 24 hours, most preferably for one hour to 16 hours. The doped polymeric material can be heated to room temperature or up to about 350° C. and the annealing can be carried out at room temperature or up to about 350° C. Preferably, the doped polymeric material can be heated to 120° C. and the annealing is carried out at 120° C. Annealing can be performed in liquid(s), in air, in other gases such as oxygen, in inert gas, in supercritical fluid(s), or in vacuum. Annealing can also be performed in ambient pressure, above ambient pressure or below ambient pressure. Annealing can also be performed while the polymeric material is immersed in liquid antioxidant, such as vitamin E, or a solution/emulsion of antioxidant(s).

Melting point: refers to the peak melting temperature of the polymeric material measured by a differential scanning calorimeter at a heating rate of 10° C. per minute when heating from −20° C. to 400° C. There may be melting of part of the polymeric material at temperatures below this temperature. Typically most semicrystalline polymeric materials start to melt at a temperature lower than the melting point; as the polymeric material is heated more crystals will melt until all crystals are molten.

Consolidation: refers generally to processes used to convert the polymeric material resin, particles, flakes, i.e. small pieces of polymeric material, into a mechanically integral large-scale solid form, which can be further processed, by, for example machining, in obtaining articles of use such as medical implants. Methods such as injection molding, extrusion, compression molding, iso-static pressing (hot or cold), etc. can be used.

In the case of UHMWPE, consolidation is most often performed by "compression molding". In some instances, consolidation can be interchangeably used with compression molding. The molding process generally involves:
  i. heating the polymeric material to be molded,
  ii. pressurizing the polymeric material while heated,
  iii. keeping at temperature and pressure, and
  iv. cooling down and releasing pressure.

Heating of the polymeric material can be done at any rate. Temperature can be increased linearly with time or in a step-wise fashion or at any other rate. Alternatively, the polymeric material can be placed in a pre-heated environment. The mold for the consolidation can be heated together or separately from the polymeric material to be molded. Steps (i) and (ii), i.e. heating and pressurizing before consolidation can be done in multiple steps and in any order. For example, polymeric material can be pressurized at room temperature to a set pressure level 1, after which it can be heated and pressurized to another pressure level 2, which still may be different from the pressure or pressure(s) in step (iii). Step (iii), where a high temperature and pressure are maintained is the 'dwell period' where a major part of the consolidation takes place. One temperature and pressure or several temperatures and pressures can be used during this time without releasing pressure at any point. For example, dwell temperatures in the range of 135 to 350° C. and dwell pressures in the range of 0.1 MPa to 100 MPa or up to 1000 MPa can be used. The dwell time can be from 1 minute to 24 hours, more preferably from 2 minutes to 1 hour, most preferably about 10 minutes. The temperature(s) at step (iii) are termed 'dwell' or 'molding' temperature(s). The pressure(s) used in step (iii) are termed 'dwell' or 'molding' pressure(s). The order of cooling and pressure release (step iv) can be used interchangeably. In some embodiments the cooling and pressure release may follow varying rates independent of each other. In some embodiments, consolidation of polymeric resin or blends of the resin antioxidant(s) are achieved by compression molding. In some embodiments, the consolidated polymeric material is fabricated through "direct compression molding" (DCM), which is compression molding using parallel plates or any plate/mold geometry which can directly result in an implant or implant preform. Preforms are generally oversized versions of implants, where some machining of the preform can give the final implant shape.

Compression molding can also be done such that the polymeric material is directly compression molded onto a second surface, for example a metal or a porous metal to result in an implant or implant preform. This type of molding results in a "hybrid interlocked polymeric material" or "hybrid interlocked medical implant preform" or "hybrid interlocked medical implant". Molding is conducted with a metal piece that becomes an integral part of the consolidated polymeric article. For example, a combination of antioxidant-containing polyethylene resin, powder, or flake and virgin polyethylene resin, powder or flake is direct compression molded into a metallic acetabular cup or a tibial base plate. The porous tibial metal base plate is placed in the mold, antioxidant blended polymeric resin, powder, or flake is added on top. Prior to consolidation, the pores of the metal piece can be filled with a waxy or plaster substance through half the thickness to achieve polyethylene interlocking through the other unfilled half of the metallic piece. The pore filler is maintained through the irradiation and subsequent processing (for example antioxidant diffusion) to prevent infusion of components in to the pores of the metal. In some embodiments, the article is machined after processing to shape an implant. In some embodiments, there is more than one metal piece integral to the polymeric article. The metal(s) may be porous only in part or non-porous. In another embodiment, one or some or all of the metal pieces integral to the polymeric article is a porous metal piece that allows bone in-growth when implanted into the human body. In one embodiment, the porous metal of the implant is sealed using a sealant to prevent or reduce the infusion of antioxidant (in diffusion steps after consolidation) into the pores during the selective doping of the implant. Preferably, the sealant is water soluble. But other sealants are also used. The final cleaning step that the implant is subjected to also removes the sealant. Alternatively, an additional sealant removal step is used. Such sealants as water, saline, aqueous solutions of water soluble polymers such as poly-vinyl alcohol, water soluble waxes, plaster of Paris, or others are used. In addition, a photoresist like SU-8, or other, may be cured within the pores of the porous metal component. Following processing, the sealant may be removed via an acid etch or a plasma etch.

In some embodiments, the polymeric material is blended with one or more antioxidants. The polymeric blend is consolidated onto a second material, preferably a porous metal, wherein the consolidation forms a hybrid interlocked polymeric material. The hybrid interlocked polymeric material is then irradiated in contact with or close to an electron scattering device comprising fibers using low energy electron beam irradiation at below, at or above the melting temperature of the polymeric material. The surfaces that face the beam may be the intended articular surfaces of a medical implant. Alternatively, a medical implant preform can be irradiated and some of the surfaces may be machined after irradiation.

Compression molding can also be done by "layered molding". This refers to consolidating a polymeric material by compression molding one or more of its resin forms, which may be in the form of flakes, powder, pellets or the like or consolidated forms in layers such that there are distinct regions in the consolidated form containing different concentrations of additives such as antioxidant(s) or cross-linking agent(s). Whenever a layered-molded polymeric material is described in the examples below and is used in any of the embodiments it can be fabricated by:

a. layered molding of polymeric resin powder or its additive blends where one or more layers contain no or low concentration of antioxidant(s) and one or more layers contain one or more additives such as antioxidants.
b. molding together of previously molded layers of polymeric material containing different or identical concentration of additives such as antioxidant(s) where one or more layers contain no additive(s) and one or more layers contain one or more additives such as antioxidants.
c. molding of UHMWPE resin powder with or without antioxidant(s) on to at least one previously molded polymeric material with or without antioxidant(s) where one or more layers contain no or low concentration of antioxidant(s) and one or more layers contain one or more additives such as antioxidant(s).

The layer or layers to be molded can be heated in liquid(s), in water, in air, in inert gas, in supercritical fluid(s) or in any environment containing a mixture of gases, liquids or supercritical fluids before pressurization. The layer or layers can be pressurized individually at room temperature or at an elevated temperature below the melting point or above the melting point before being molded together. The temperature at which the layer or layers are pre-heated can be the same or different from the molding or dwell temperature(s). The temperature can be gradually increased from pre-heat to mold temperature with or without pressure. The pressure to which the layers are exposed before molding can be gradually increased or increased and maintained at the same level.

During molding, different regions of the mold can be heated to different temperatures. The temperature and pressure can be maintained during molding for 1 second up to 1000 hours or longer. During cool-down under pressure, the pressure can be maintained at the molding pressure or increased or decreased. The cooling rate can be 0.0001° C./minute to 120° C./minute or higher. The cooling rate can be different for different regions of the mold. After cooling down to about room temperature, the mold can be kept under pressure for 1 second to 1000 hours. Or the pressure can be released partially or completely at an elevated temperature.

Crosslinking: Polymeric Materials, for example, UHMWPE can be cross-linked by a variety of approaches, including those employing cross-linking chemicals (such as peroxides and/or silane) and/or irradiation. Cross-linked UHMWPE can be obtained according to the teachings of U.S. Pat. Nos. 5,879,400 and 6,641,617, PCT International Application Publication Nos. WO 2001/05337 and WO 97/29793, and U.S. Patent Application Publication No. 2003/0149125, the entirety of which are hereby incorporated by reference.

The term 'substantial cross-linked' refers to the state of a polymeric material where polymer swelling in a good solvent is significantly reduced from the uncross-linked state. For instance, the cross-link density of polyolefins, such as polyethylene is measured by swelling a roughly 3×3×3 mm cube of polymeric material in xylene. The samples are weighed before swelling in xylene at 130° C. for 2 hours and they are weighed immediately after swelling in xylene. The amount of xylene uptake is determined gravimetrically, then converted to volumetric uptake by dividing by the density of xylene; 0.75 g/cc. By assuming the density of polyethylene to be approximately 0.94 g/cc, the volumetric swell ratio of cross-linked UHMWPE is then determined. The cross-link density is calculated by using the swell ratio as described in Oral et al., *Biomaterials* 31: 7051-7060 (2010) and is reported in mol/m$^3$. The term 'highly cross-linked' refers generally to the state of the polymeric material where there is further cross-linking and the cross-link density is higher than that of 'substantially cross-linked' polymeric material. The term 'cross-linked' refers to the state of polymeric material that is cross-linked to any level, for instance substantial cross-linked or highly cross-linked states.

The term 'wear' refers to the removal of material from the polymeric material during articulation or rubbing against another material. For UHMWPE, wear is generally assessed gravimetrically after an initial creep deformation allowance in number of cycles of motion. The term 'wear resistant' refers to the state of a polymeric material where it has low wear. For example, the wear rate is tested on cylindrical pins (diameter 9 mm, length 13 mm) on a bidirectional pin-on-disc wear tester in undiluted bovine calf serum at 2 Hz in a rectangular pattern (5 mm×10 mm) under variable load with a maximum of 440 lbs as described in Bragdon et al., *J Arthroplasty* 16: 658-665 (2001)). Initially, the pins are subjected to 0.5 million cycles (MC), after which they are tested to 1.25 million cycles with gravimetric measurements approximately every 0.125 MC. The wear rate is determined by the linear regression of the weight loss as a function of number of cycles from 0.5 to 1.25 MC. The term "highly wear resistant" refers to the state of a polymeric material with a wear rate of less than 3 mg/million-cycles under these conditions.

The term "heating" refers to the thermal treatment of the polymer at or to a desired heating temperature. In one aspect, heating can be carried out at a rate of about 10° C. per minute to the desired heating temperature. Heating can be carried out at a rate between 0.001° C./min to 1000° C./min, or 0.1° C./min and 100° C./min or at about 0.2, 0.3, 0.4, 0.5, 0.6, 0.7, 0.8, 0.9, 1° C./min or rates between 1 and 20° C./min in 0.1° C. intervals. In another aspect, the heating can be carried out at the desired heating temperature for a desired period of time. Heating can be performed at a temperature between about −80° C. and about 500° C. or at about 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., 220° C., 225° C., 230° C., 235° C., 240° C., 245° C., 250° C., 255° C., 260° C., 265° C., 270° C., 275° C., 280° C., 285° C., 290° C., 295° C., 300° C., 305° C., 310° C., 315° C., or 320° C. In other words, heated polymers can be continued to heat at the desired temperature, below or above the melting point, for a desired period of time. Heating time at or to a desired heating temperature can be at least 1 minute to 48 hours to several weeks long. In one aspect, the heating time is about 1 hour to about 24 hours. For example, the heating is continued for at least for 1 second, 1 minute, 10 minutes, 20 minutes, 30 minutes, one hour, two hours, five hours, ten hours, 24 hours, or more. Or the heating is continued from 10 minutes to 24 hours or more in 10 minute intervals. Cooling after heating can be done at any rate. For example, cooling rate can be about 0.0001° C./min to 1000° C./min, or about 0.1° C./min to 10° C./min, or about 1° C./min or about 2° C./min.

In another aspect, the heating can be carried out for any time period as set forth herein, before or after irradiation. Heating temperature refers to the thermal condition for heating in accordance with the invention. Heating can be performed at any time in a process, including during, before and/or after irradiation. Heating can be done with a heating element. Other sources of energy include the environment and irradiation.

The term "high temperature melting" refers to thermal treatment of the polymer or a starting material to a temperature between about 200° C. and about 500° C. or more, for example, temperature of about 200° C., about 250° C., about 280° C., about 300° C., about 320° C., about 350° C., about 380° C., about 400° C., about 420° C., about 450° C., about 480° C. or more. Heating time at "high temperature melting" can be at least 30 minutes to 48 hours to several weeks long. In one aspect the "high temperature melting" time is continued for about 1 minute to about 48 hours or more. For example, the heating is continued for at least for one minute, 10 minutes, 20 minutes, 30 minutes, one hour, two hours, five hours, ten hours, 24 hours, or more. High temperature melting can be done in inert gas, in air, or in supercritical fluids.

The term "annealing" refers to heating or a thermal treatment condition of the polymers in accordance with the invention. Annealing generally refers to continued heating of the polymers at a desired temperature below its peak melting point for a desired period of time, but in the invention refers to the thermal treatment of polymeric material at any desired temperature for a period of time. Annealing time can be at least 1 minute to several weeks long. In one aspect the annealing time is about 4 hours to about 48 hours, preferably 24 to 48 hours and more preferably about 24 hours. "Annealing temperature" refers to the thermal condition for annealing in accordance with the invention.

The term "packaging" refers to the container or containers in which a medical device is packaged and/or shipped. Packaging can include several levels of materials, including bags, blister packs, heat-shrink packaging, boxes, ampoules, bottles, tubes, trays, or the like or a combination thereof. A single component may be shipped in several individual types of package, for example, the component can be placed in a bag, which in turn is placed in a tray, which in turn is placed in a box. The whole assembly can be sterilized and shipped. The packaging materials include, but are not limited to, vegetable parchments, multi-layer polyethylene, Nylon 6, polyethylene terephthalate (PET), and polyvinyl chloride-vinyl acetate copolymer films, polypropylene, polystyrene, and ethylene-vinyl acetate (EVA) copolymers.

In any of the embodiments, the final implants are packaged and sterilized. Sterilization can be achieved by gas sterilization methods or by irradiation, for example gamma or electron beam irradiation. Sterilization can be done under vacuum, in inert gas environment, in air, or any combination thereof.

The term "non-permanent device" refers to what is known in the art as a device that is intended for implantation in the body for a period of time shorter than several months. Some non-permanent devices could be in the body for a few seconds to several minutes, while other may be implanted for days, weeks, or up to several months. Non-permanent devices include catheters, tubing, intravenous tubing, and sutures, for example. The term "permanent device" refers to what is known in the art that is intended for implantation in the body for a period longer than several months. Permanent devices include medical devices, for example, acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, and vascular grafts. The term "medical implant" refers to what is known in the art as a device intended for implantation in animals or humans for short or long term use. The medical implants, according to an aspect of the invention, comprises medical devices including acetabular liner, shoulder glenoid, patellar component, finger joint component, ankle joint component, elbow joint component, wrist joint component, toe joint component, bipolar hip replacements, tibial knee insert, tibial knee inserts with reinforcing metallic and polyethylene posts, intervertebral discs, sutures, tendons, heart valves, stents, vascular grafts.

The term 'high pressure crystallized' refers to the state of a polymeric material where the polymeric material has been taken to above its glass transition or melting temperature where it was allowed to obtain a partially or totally disordered conformation, maintained at these temperatures and pressures, then cooled under pressures higher than the ambient pressure to obtain a partly or totally ordered conformation such as a semi-crystalline state.

Under some conditions where the temperatures and pressures where the polymeric material are in certain ranges, the polymeric material can crystallize in a conformation different than if it was crystallized at or about ambient pressure. For ultrahigh molecular weight polyethylene, consolidation by compression molding typically employs temperatures around 170 to 210° C. and pressures around 10-20 MPa. However, crystallization at temperatures above about 160° C. and pressures above about 200 MPa may result in the formation of extended chain crystals. When extended chain crystals are formed, overall crystallinity is often increased and fatigue strength can be increased as well. The presence of a lipophilic compound such as vitamin E during the high pressure crystallization process may increase the extent of formation of the extended chain crystals (crystallinity) and the fatigue strength (Oral et al., *Biomaterials* 30: 1870-1880 (2009)).

High pressure crystallization can be done at temperatures from 140 to 340° C. or above, preferably from 160 to 240° C. High pressure crystallization can be done at 2 to 2000 MPa or above, preferably from 5 to 20 MPa or from 250 to 400 MPa.

Cooling and heating during the high pressure crystallization process can be done at any rate, for example at 0.01 to 1000° C./min, preferably from 1 to 10° C./min. Heating and cooling and pressurization can be done simultaneously or in sequence in any order.

The term 'high temperature melting' refers to melting a polymeric material at temperatures above about 200° C. Melting a consolidated polymeric material such as UHMWPE has been shown to increase the toughness of the polymeric materials mainly by increasing elongation (Fu et al., *Polymer* 51: 2721-2731 (2010)).

High temperature can be done at temperatures from 200 to 500° C. and above, preferably from 250 to 320° C. The toughness that is a result of the high temperature melting process is highly dependent on the time that the polymeric material is annealed at the melting temperature or temperature(s). Thus, the high temperature melting can be done for 1 minute to 36 hours or more, preferably from 2 to 12 hours.

Cooling and heating during the high temperature melting process can be done at any rate, for example at 0.01 to 1000° C./min, preferably from 1 to 10° C./min. Heating and cooling and pressurization can be done simultaneously or in sequence in any order. Methods of high temperature melting are described in Muratoglu et al. (PCT International Application Publication No. WO 2010/096771).

The term 'electron scattering device' refers to a material or materials or combination of different materials such as metal or polymers of one or more morphologies such as fibers, yarn, wool, strips, woven fabrics, brushes which can act to scatter electrons incident on their surfaces. The morphologies are changed to modulate the surface area available for incident electrons among other things. Electron scattering is the process by which electrons deviate from their original trajectory.

EXAMPLES

Various methods of making cross-linked polymeric materials containing antioxidants according to the invention are described in more details in the following illustrative examples. Although the examples may represent only selected embodiments of the invention, it should be understood that the following examples are illustrative and not limiting.

Example 1. Irradiation of Vitamin E-Blended UHMWPE Using Low Energy Electrons without Shielding Medical grade GUR1050 UHMWPE (Orthoplastics, UK) resin flakes were blended with vitamin E. Vitamin E-blended UHMWPE (with 0.1 wt. % Vitamin E) was compression molded into pucks, then machined into rectangular blocks (20×30×10.5 mm). Three of each block was irradiated by placing on a belt under the electron beam and conveying the samples back and forth under the beam. The samples were placed with their 10.5 by 30 mm side normal to the incident beam. The blocks were irradiated with electron beam energies of 0.8 MeV, 1.2 MeV, 1.6 MeV and 2.4 MeV to a total dose of 150 kGy. The dose rate was different in each case and ranged from 5 kGy/pass to 25 kGy/pass.

The blocks were cut in half along the length. A 150 microns-thick inner surface was microtomed and analyzed by FTIR. Spectra were collected as an average of 32 scans from the edge of the thin film that corresponded to the irradiated surface towards the edge of the thin film that corresponded to the backside at 100-500 micron intervals. A transvinylene index (TVI) was calculated by taking the area under the absorbance peak at 965 $cm^{-1}$ (950 to 980 $cm^{-1}$) and normalizing it to a crystalline peak of polyethylene at an absorbance of 1895 $cm^{-1}$ (1850 to 1985 $cm^{-1}$) after subtracting the baselines.

TABLE 2

Surface depth and penetration limit for 150-kGy irradiated 0.1 wt % vitamin E-blended UHMWPE irradiated at different electron beam energy

| Beam energy | Surface depth (>0.13 for 150 kGy) (mm.) | Penetration Limit (=0.02) (mm.) | Gradient Depth (mm.) | Surface Average TVI |
|---|---|---|---|---|
| 0.8 MeV | 2.0 | 2.6 | 0.6 | 0.183 |
| 1.2 MeV | 3.4 | 4.4 | 1.0 | 0.170 |
| 1.6 MeV | 4.9 | 6.6 | 1.7 | 0.157 |
| 2.4 MeV | 8.1 | 10.6 | 2.5 | 0.162 |

Figure 11:
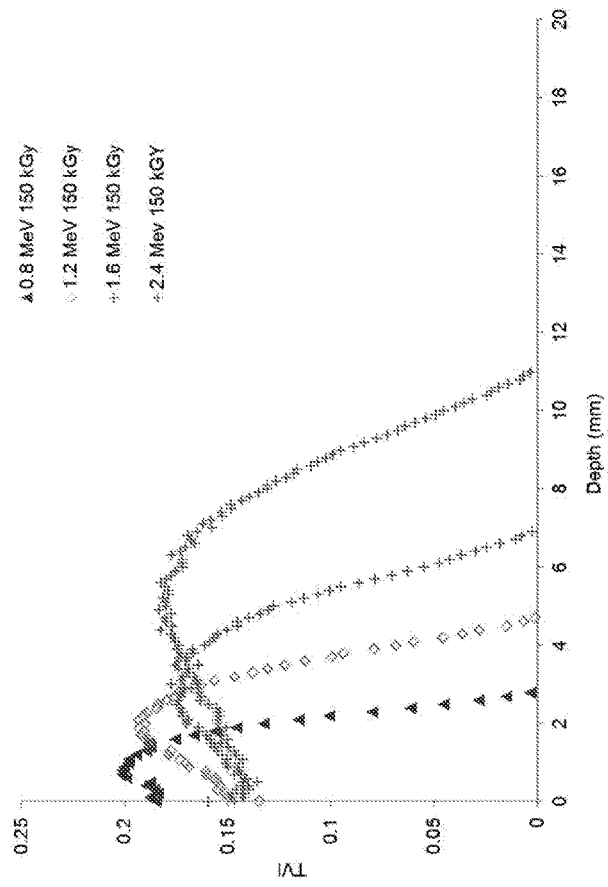
FIG. 11 shows transvinylene index (TVI) as a function of depth away from the irradiated surface for 0.1 wt % vitamin E-blended UHMWPE irradiated at different electron beam energy.

The results showed that the TVI profiles of the irradiated UHMWPEs changed significantly with changing the energy of the beam (see FIG. 11). A surface average TVI index was calculated by averaging the readings above an index level of 0.13 and a crosslinking gradient was calculated from the depth where the index reached 0.13 to an index of 0.02, which was considered the penetration limit. Table 2 shows these results.

Irradiation with 0.8 MeV electrons resulted in a highly cross-linked surface (TVI=0.183±0.10) and the narrowest gradient depth (0.6 mm) for a total penetration of 2.6 mm.

Example 2. Irradiation of Vitamin E-Blended UHMWPE Using Low Energy Electrons with Shielding Medical grade GUR1050 UHMWPE (Orthoplastics, UK) resin flakes were blended with vitamin E. Vitamin E-blended UHMWPE (with 0.1 wt % vitamin E) was compression molded into pucks, then machined into rectangular blocks (20×30×10.5 mm). Three of each block was placed on a belt under the electron beam (Van-de-Graf generator, High Voltage Research Laboratory, MIT, Cambridge, Mass., USA) and were covered with flat shields machined from aluminum or copper at different thickness (see Table 3). The samples were conveyed back and forth under the beam. The samples were placed with their 10.5 by 30 mm side normal to the incident beam. The blocks were irradiated with electron beam energies of 0.8 MeV, 1.2 MeV, 1.6 MeV and 2.4 MeV to a total dose of 150 kGy. The dose rate was different in each case and range from 5 kGy/pass to 25 kGy/pass.

TABLE 3

Surface depth, penetration limit, gradient depth and surface TVI average for vitamin E-blended UHMWPE irradiated at different beam energy with shields.

| Thickness and shield material | Beam energy | Surface depth (TVI > 0.13 for 150 kGy) | Full Depth (TVI > 0.02) | Gradient Depth | Surface Average |
|---|---|---|---|---|---|
| | 0.8 MeV | 2.0 | 2.6 | 0.6 | 0.183 |
| 0.2 mm Cu | 1.2 MeV | 2.8 | 4.0 | 1.2 | 0.159 |
| 0.3 mm Al | 1.2 MeV | 2.3 | 3.6 | 1.3 | 0.165 |
| 0.7 mm Al | 1.6 MeV | 2.7 | 4.6 | 1.9 | 0.164 |
| 2 mm Al | 2.4 MeV | 2.0 | 5.3 | 3.3 | 0.157 |

Figure 12:
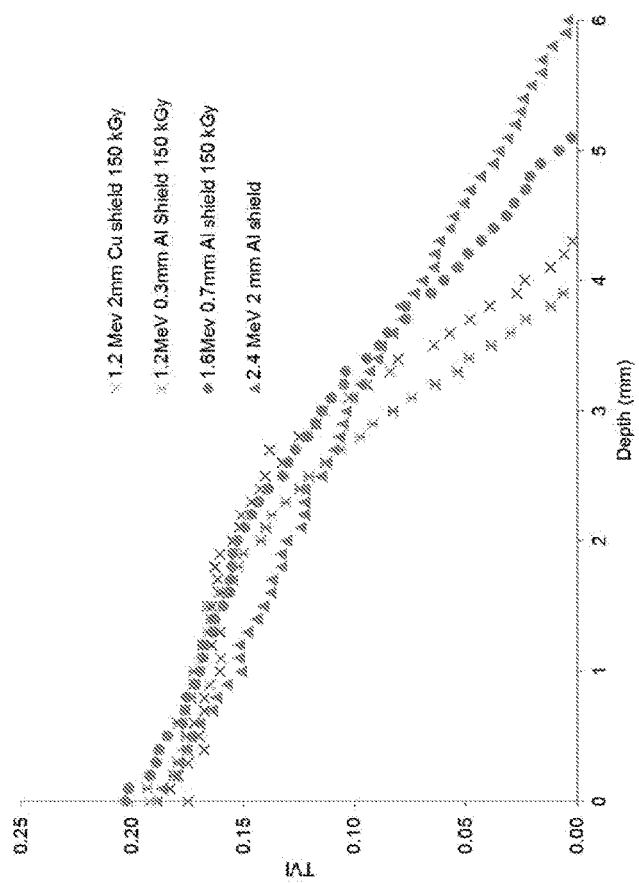
FIG. 12 shows transvinylene index (TVI) profiles of 0.1 wt % vitamin E-blended UHMWPE irradiated at different electron energy using shields.

The blocks were cut in half along the length. A 150 microns-thick inner surface was microtomed and analyzed by FTIR. Spectra were collected as an average of 32 scans from the edge of the thin film that corresponded to the irradiated surface towards the edge of the thin film that corresponded to the backside at 100-500 micron intervals. A transvinylene index (TVI) was calculated by taking the area under the absorbance peak at 965 cm$^{-1}$ (950 to 980 cm$^{-1}$) and normalizing it to a crystalline peak of polyethylene at an absorbance of 1895 cm$^{-1}$ (1850 to 1985 cm$^{-1}$) after subtracting the baselines. A surface depth of 2-3 mm was achieved using a combination of different shield materials and thicknesses for samples irradiated at different beam energies (see Table 3). The TVI profiles were significantly different (see FIG. 12). It was possible to obtain sharp transitions from the highly cross-linked to the uncross-linked UHMWPE using low energy irradiation.

Example 3. Wear Testing of Vitamin E-Blended UHMWPE Irradiated with Low Energy Electrons Medical grade GUR1050 UHMWPE (Orthoplastics, UK) resin powder were blended with vitamin E. Vitamin E-blended UHMWPE (0.1 or 0.2 wt %) resin powders were compression molded into pucks, then machined into cylindrical pins (9 mm diameter×13 mm length). The pins were irradiated by placing on a belt under the electron beam and conveying the samples back and forth under the beam incident on the flat surface of the pins (to be tested subsequently for wear when articulating against a metal counterface). The 0.1 wt % vitamin E-blended pins were irradiated with electron beam energy of 0.8 MeV to a total dose of 150 kGy and the 0.2 wt % vitamin E-blended pins were irradiated with electron beam energy of 0.8 MeV to a total dose of 200 kGy. The dose rate was different in each case (~5 kGy/pass). One 0.1 wt % vitamin E-blended, consolidated UHMWPE block was irradiated with electron beam energy of 3.0 MeV to a total dose of 150 kGy, then machined into pins.

Wear testing was done on a custom-designed bidirectional pin-on-disc (POD) tester in undiluted bovine serum. The pins were tested at 2 Hz under a peak load of 440 lbs for 1.2 million cycles (MC). They were weighed and the wear was determined gravimetrically at 500,000 cycles and every 157,000 cycles after that. Wear rate was determined by a linear regression of weight loss as a number of cycles from 500,000 cycles to 1.2 million cycles.

One set of pins were tested as irradiated, another set was tested after machining 1 mm of the surface and yet another set was tested after machining 2 mm of the surface away. The wear rates of 0.1 wt % vitamin E-blended, 150 kGy irradiated (0.8 MeV) UHMWPE after no machining, after 1 mm machining and after 2 mm machining were 1.12±0.15, 0.33±0.02 and 1.12±0.13 mg/MC, respectively. The wear rates for 0.2 wt % vitamin E-blended, 200 kGy irradiated (0.8 MeV) UHMWPEs after no machining, after 1 mm machining and after 2 mm machining were 0.95±0.03, 0.28±0.06 and 1.18±0.36 mg/MC, respectively. The decrease in the wear rate below the surface was attributed to the ~10% increase in crosslinking as measured by the TVI below the surface in materials irradiated with low energy electrons (see FIG. 3).

The wear rate of the 0.1 wt % vitamin E-blended and 150 kGy uniformly irradiated (3 MeV) pins was 0.98±0.11 mg/MC.

These results showed that vitamin E-blended UHMWPEs which were subsequently irradiated with low energy electrons resulted in a cross-linked surface with high wear resistance.

Figure 13:
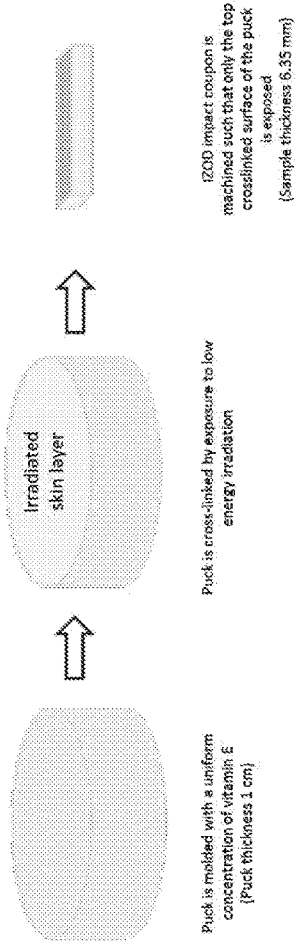
FIG. 13 is a schematic depiction of the preparation of surface crosslinked coupons for IZOD impact testing.

Example 4. Impact Testing of Vitamin E-Blended UHMWPE Irradiated with Low Energy Electrons Medical grade GUR1050 UHMWPE (Orthoplastics, UK) resin flakes were blended with vitamin E. Vitamin E-blended UHMWPE (with 0.1 wt % vitamin E) was compression molded into pucks (10 cm diameter, ~1 cm thickness). The pucks were irradiated by placing on a belt under the electron beam (Van-de-Graf generator, High Voltage Research Laboratories, MIT, Cambridge, Mass.) and conveying the samples back and forth under the beam. The irradiated pucks were then machined into impact specimens per ASTM D256, where the impact specimens contained the irradiated top surface (see FIG. 13). The specimen size was 6.35 mm×12.7 mm×63.5 mm. Notching and double notched IZOD impact testing was performed according to ASTM F648 at Orthoplastics Ltd. (Lancashire, UK).

The impact strength of the 0.1 wt % vitamin E-blended UHMWPE irradiated with electron beam energy of 0.8 MeV to a radiation dose of 150 kGy was 88±1.4 kJ/m$^2$, that of 0.1 wt % vitamin E-blended UHMWPE irradiated with a beam energy of 1.2 MeV was 68±4 kJ/m$^2$, that of 0.1 wt % vitamin E-blended UHMWPE irradiated with a beam energy of 1.6 MeV was 60±4 kJ/m$^2$, that of 0.1 wt % vitamin E-blended UHMWPE irradiated with a beam energy of 2.4 MeV was 53±2 kJ/m$^2$ and the impact strength of the 0.1 wt % vitamin E-blended UHMWPE irradiated with electron beam energy of 3.0 MeV to a radiation dose of 150 kGy was 56±1 kJ/m$^2$. These results showed that limiting crosslinking to the surface of the implant by using low electron energy during irradiation improved the impact strength significantly (0.8 MeV vs. 3 MeV; p=0.0006). Statistical significance was determined by using a Student's t test for two-tailed distributions with unequal variance.

Example 5. Antioxidant Diffusion into Irradiated Antioxidant Blends

Medical grade GUR1050 UHMWPE (Orthoplastics, UK) resin flakes were blended with vitamin E. Vitamin E-blended UHMWPE (with 0.1 wt % vitamin E) was compression molded into pucks (10 cm diameter, ~6.4 mm thickness). The pucks were irradiated by placing on a belt under the electron beam (Van-de-Graf generator, High Voltage Research Laboratories, MIT, Cambridge, Mass.) and conveying the samples back and forth under the beam. The electron beam energy was 0.8 MeV and the total irradiation dose was 150 kGy in multiple passes.

The pucks were machined into 10×10×6 mm samples with one surface coinciding with the top surface of the puck during irradiation. Three samples each were analyzed (1) as is, (2) after doping with vitamin E pre-heated to 110° C. for 1 hour and (3) after doping in vitamin E pre-heated to 110° C. for 1 hour and homogenization in argon at 130° C. for 24 hours.

To measure the diffusion profile of vitamin E in UHMWPE, a cross-section was cut out of the doped sample (100-150 μm) using an LKB Sledge Microtome (Sweden). The thin cross-section was then analyzed using a BioRad UMA 500 infrared microscope (Natick, Mass., USA). Infrared spectra were collected with an aperture size of 50×50 μm as a function of depth away from one of the edges that coincided with the free surface of the sample. The absorbance at 1260 cm$^{-1}$ was characteristic of α-Tocopherol (also Vitamin E) and polyethylene did not absorb near these frequencies. For polyethylene, the 1895 cm$^{-1}$ wavenumber for the $CH_2$ rocking mode was a typical choice as an internal reference. We calculated a vitamin E index as the ratio of the integrated absorbances of 1260 cm$^{-1}$ (from 1245 to 1275 cm$^{-1}$) and 1895 cm$^{-1}$ (from 1850 to 1985 cm$^{-1}$) after subtracting the corresponding baselines.

Figure 14:
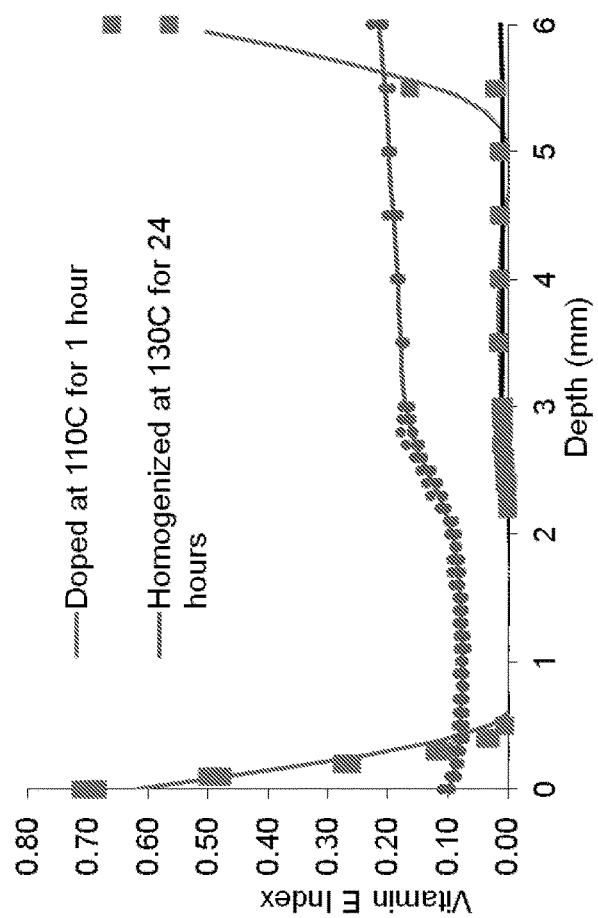
FIG. 14 shows the vitamin E concentration profiles of 0.1 wt % vitamin E-blended, low energy irradiated (0.8 MeV) and vitamin E diffused UHMWPEs after doping (rectangles in FIG. 14) and after further homogenization (circles in FIG. 14).

The penetration of vitamin E into 0.1 wt % vitamin E-blended, irradiated (0.8 MeV) and vitamin E-diffused UHMWPE is shown in FIG. 14. The average vitamin E index of 0.1 wt % vitamin E blended UHMWPE after 150 kGy irradiation at 0.8 MeV was −0.005±0.003 in the surface 2.5 mm cross-linked region and 0.009±0.001 in the uncross-linked region from 2.6 to 6 mm. After doping in vitamin E at 110° C. for 1 hour, the penetration depth (vitamin E index>0.02) was 0.5±0.0 mm from the surface, and after doping and homogenization at 130° C. for 24 hours, the penetration was throughout the sample. The average vitamin E index of the sample doped at 110° C. for 1 hour was 0.06±0.00 in the first 2.5 mm of the sample. The average vitamin E index of the sample doped at 110° C. for 1 hour and homogenized at 130° C. for 24 hours was 0.07±0.02.

These results showed that a uniformly antioxidant-blended UHMWPE could be irradiated by low energy electrons, thereby forming an antioxidant-containing UHMWPE with a spatial control of cross-linking and diffused with additional antioxidant after irradiation to achieve high antioxidant concentration on the surface or a relatively uniform antioxidant concentration on the surface. In this manner, a surface cross-linked UHMWPE with high wear resistance (Example 3), high impact strength (Example 4) and high vitamin E content was achieved.

Example 6. Antioxidant Diffusion into Irradiated Antioxidant Blends from Reservoir Medical grade GUR1050 UHMWPE (Orthoplastics, UK) resin flakes are blended with vitamin E. Vitamin E-blended UHMWPE (with 0.3 wt % vitamin E) is compression molded into medical implant preforms. The preforms are irradiated with the desired surfaces facing the electron beam by an electron beam with 0.8 MeV energy electrons and the total irradiation dose is 150, or 200 kGy.

The preforms are doped with vitamin E pre-heated to 120° C. for 1 hour and homogenized in argon at 130° C. for 24 hours.

The vitamin E-doped and homogenized medical implant preforms are machined from the surfaces to form a medical implant with the desired shape. The final medical implant is packaged and sterilized by gamma irradiation to as dose of 25, 40, or 50 kGy.

Example 7. Diffusion of Vitamin E into Vitamin E-Blended UHMWPE

Medical grade GUR1050 UHMWPE (Orthoplastics, UK) resin flakes were blended with vitamin E. Vitamin E-blended UHMWPE (with 0.1 or 0.2 wt % vitamin E) was compression molded into pucks (10 cm diameter, ~10 mm thickness).

Some of the pucks were machined into cubes (1×1×1 cm) without further treatment. Some pucks were irradiated by placing on a belt under the electron beam (Van-de-Graf generator, High Voltage Research Laboratories, MIT, Cambridge, Mass.) and conveying the samples back and forth under the beam. The electron beam energy was 3 MeV and the total irradiation dose was 50, 100 or 150 kGy in 25 kGy/pass. Then, the irradiated pucks were also machined into cubes (1×1×1 cm).

Three samples each were analyzed after doping in vitamin E pre-heated to 120° C. for 4 hours (n=3 each).

To measure the diffusion profile of vitamin E in UHMWPE, a cross-section was cut out of the doped sample (100-150 μm) using an LKB Sledge Microtome (Sweden). The thin cross-section was then analyzed using a BioRad UMA 500 infrared microscope (Natick, Mass.). Infrared spectra were collected with an aperture size of 50×50 μm as a function of depth away from one of the edges that coincided with the free surface of the sample. We calculated a vitamin E index as the ratio of the integrated absorbances of 1260 cm$^{-1}$ (from 1245 to 1275 cm$^{-1}$) and 1895 cm$^{-1}$ (from 1850 to 1985 cm$^{-1}$) after subtracting the corresponding baselines.

The penetration of vitamin E into vitamin E-diffused, unirradiated UHMWPE was calculated as the depth from the surface of the sample when the vitamin E index decreased to below 0.02. Thus, the penetration depth into virgin, unirradiated UHMWPE at 120° C. in 4 hours was 1.57±0.12 mm and that into 0.1 wt % vitamin E-blended UHMWPE was 1.93±0.06 mm.

The cross-link density of 50, 100 and 150 kGy irradiated UHMWPEs was calculated by swelling in xylene. The cross-link density of the surface was measured using small sections (approximately 3×3×3 mm, n=6 each) prepared manually by cutting with a razor blade. The samples were placed in 25 mL of pre-heated xylene 130° C. in an oil bath and were allowed to swell for 2 hours. The dry sample weight and the swollen sample weight were measured in sealed containers before and after xylene immersion to determine a gravimetric swell ratio. The gravimetric swelling ratio was converted to a volumetric swelling ratio using the density of the dry polymer as 0.94 g/cm$^3$ and the density of xylene at 130° C. as 0.75 g/cm$^3$. The cross-link density of the samples (n=3 each) was calculated using the following equations:

$$d_x = \frac{\ln(1 - q_{eq}^{-1}) + q_{eq}^{-1} + X q_{eq}^{-2}}{V_1(q_{eq}^{-1/3} - q_{eq}^{-2})} \quad \text{(Eq. 1)}$$

$$X = 0.33 + \frac{0.55}{q_{eq}} \quad \text{(Eq. 2)}$$

where the specific volume of xylene, $V_1$, was 136 cm$^3$/mol.

Figure 15:
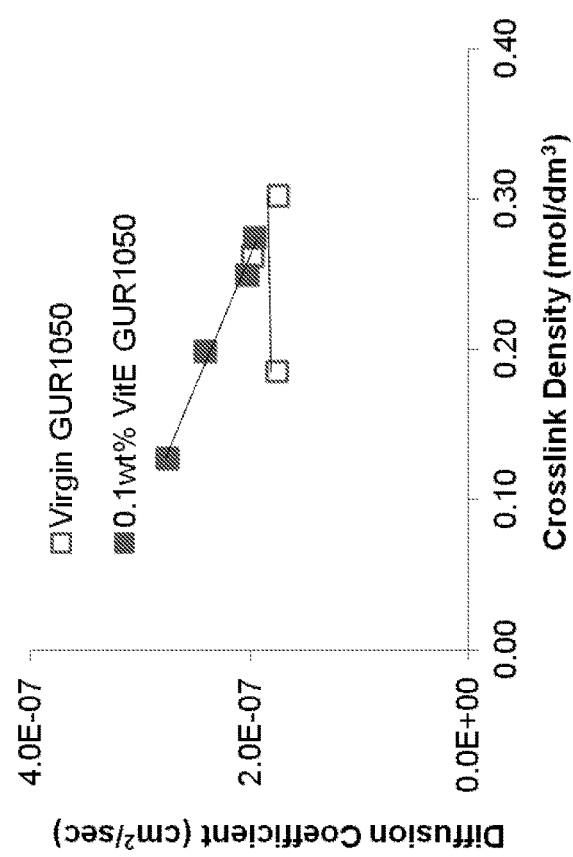
FIG. 15 shows diffusion coefficients of cross-linked virgin and 0.1 wt % vitamin E blends as a function of cross-link density.

The diffusion coefficients of vitamin E in cross-linked UHMWPEs calculated from the diffusion profiles as described in Oral et al., "Diffusion of vitamin E in UHMWPE", *Biomaterials* 28: 5225-5237 (2007) were plotted against cross-link density (see FIG. 15).

These results showed that diffusion into a previously vitamin E-blended UHMWPE can be faster than into virgin UHMWPE both in unirradiated and irradiated forms.

Example 8. Grafting of Vitamin E in UHMWPE by Irradiation

Medical grade GUR1050 UHMWPE (Orthoplastics, UK) resin flakes were blended with vitamin E. Vitamin E-blended UHMWPE flakes (with 0.3, 0.5, 1.0 or 2.0 wt % vitamin E) were compression molded into pucks (10 cm diameter, ~10 mm thickness).

Pucks were irradiated by electron beam (Iotron, Vancouver, BC, Canada) and conveying the samples back and forth under the beam. The electron beam energy was 10 MeV and the total irradiation dose was 25, 100, 150, 175 and 200 kGy in 25 kGy/pass. Then, the irradiated pucks were also machined into cubes (1×1×1 cm).

To measure the diffusion profile of vitamin E in UHMWPE, a cross-section was cut out of the irradiated sample (100-150 µm) using an LKB Sledge Microtome (Sweden). The thin cross-section was then analyzed using a BioRad UMA 500 infrared microscope (Natick, Mass.). Infrared spectra were collected with an aperture size of 50×50 µm as a function of depth away from the free surfaces of the sample. We calculated a vitamin E index as the ratio of the integrated absorbances of 1260 $cm^{-1}$ (from 1245 to 1275 $cm^{-1}$) and 1895 $cm^{-1}$ (from 1850 to 1985 $cm^{-1}$) after subtracting the corresponding baselines.

Some thin sections (150 µm) were boiled in hexane overnight and then dried in vacuum for 24 hours. They were analyzed by FTIR for vitamin E content as described above. The graft percentage was calculated as the ratio of the vitamin E index after extraction to that before extraction.

The graft ratio of 0.3, 0.5, 0.75, 1 and 2 wt % vitamin E-blended UHMWPEs irradiated to 150 kGy were 88, 81, 47, 21 and 10%, respectively. These results showed that there is a significant amount of unextractable vitamin E in irradiated vitamin E-blended UHMWPEs and also that the graft ratio increased with decreasing concentrations of vitamin E.

In a related experiment, medical grade GUR1050 UHMWPE (Orthoplastics, UK) resin flakes were blended with vitamin E. Vitamin E-blended UHMWPE flakes (with 1.0 wt % vitamin E) was compression molded into pucks (10 cm diameter, ~10 mm thickness).

Pucks were irradiated by electron beam (High Voltage Research Laboratories, MIT, Cambridge, Mass.) and conveying the samples back and forth under the beam. The electron beam energy was 3 MeV and the total irradiation dose was 25, 50, 75, 100, 125 and 150 kGy in 25 kGy/pass. Some samples were irradiated at room temperature (cold irradiated) and some samples were pre-heated to 120° C. in an air convention oven in insulation for 2 hours and then irradiated immediately (warm irradiated).

Figure 16:
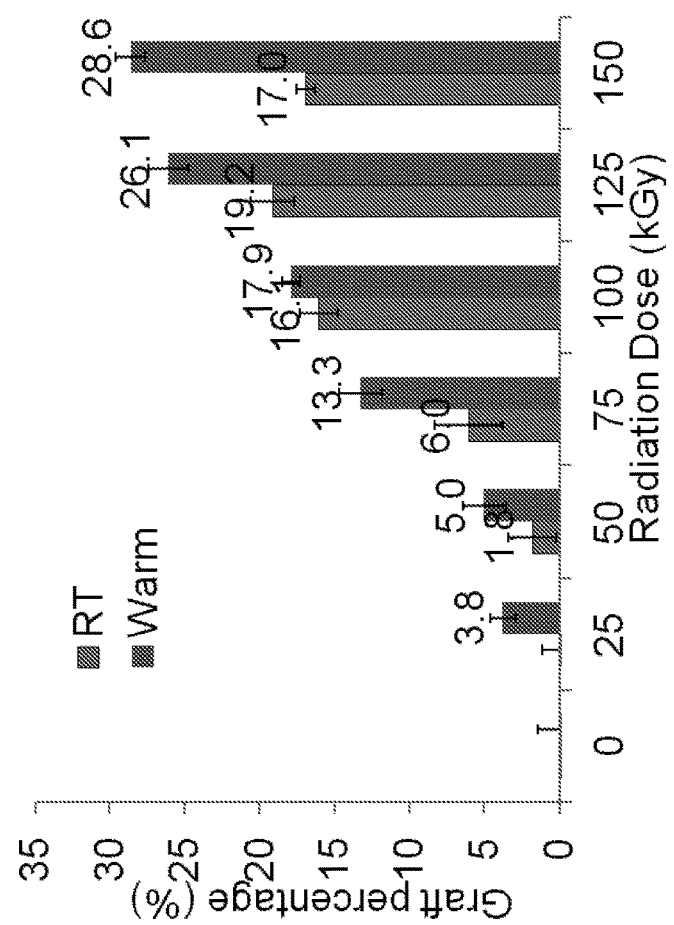
FIG. 16 shows vitamin E graft percentage as measured by hexane extraction was higher for 1 wt % vitamin E blended and warm irradiated UHMWPEs (right bar) compared to those of 1 wt % vitamin E-blended UHMWPE irradiated at room temperature (left bar).

The graft percentage of vitamin E in warm irradiated UHMWPEs was consistently higher than those for cold irradiated UHMWPEs (see FIG. 16).

Example 9. The Relative Oxidation Resistance of Blended, Irradiated and Irradiated, Diffused UHMWPEs Medical grade UHMWPE (GUR1020 and GUR1050; Orthoplastics, Lanchasire, UK) were used. GUR1050 consolidated stock was irradiated to 100-kGy by gamma irradiation. Medical implant preforms were machined from the irradiated stock. The preforms were doped in vitamin E, then homogenized at 120-130° C. Then, implants were machined from the antioxidant-diffused preforms and they were gamma sterilized. Another consolidated stock of 0.1 wt % vitamin E blended GUR1020 UHMWPE gamma irradiated to 120 kGy.

Cubes (1×1×1 cm) were machined out of the prepared materials. The cubes were doped in squalene, a pro-oxidant (Sigma, St. Louis, Mo., USA) for 2 or 20 hours at 120° C. The samples doped for 2 hours are called low pro-oxidant' and the samples doped for 20 hours are called 'high pro-oxidant'. All samples were aged in a pressure vessel in 5 atm. of oxygen at 70° C. for 9, 14 or 30 days. The cubes were then cut at the center and microtomed into 150 µm sections, by using an LKB Sledge Microtome (Sweden), extracted in ~200 ml refluxing hexane for 16 hours, vacuum dried, and scanned by using an UMA-500 FTIR microscope (Bio-Rad Laboratories, Natick, Mass.) from 400 to 4000 $cm^{-1}$ across the thin sections with a step length of 100 µm for 2 mm from the surface and 500 µm for the remainder of the thin section. The extent of oxidation was characterized by an oxidation index, which was calculated by normalizing the absorbance at 1715 $cm^{-1}$ (1685 to 1780 $cm^{-1}$) against the absorbance at 1370 $cm^{-1}$ (1330 to 1390 $cm^{-1}$). An average surface oxidation index was calculated by taking the average of the oxidation indices in the first 1.5 mm of the sample.

Figure 17:
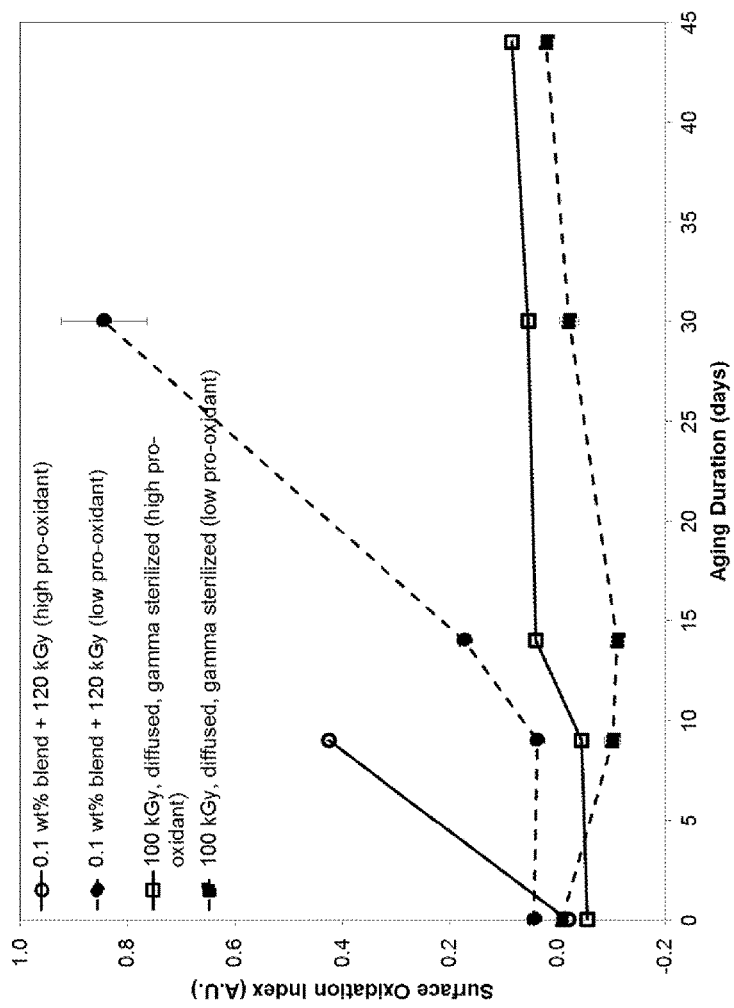
FIG. 17 shows the comparison of the oxidative resistance of a vitamin E blended, irradiated UHMWPE (0.1 wt %+120 kGy gamma irradiation) to an irradiated, vitamin E diffused, gamma sterilized UHMWPE (100 kGy gamma irradiation of virgin UHMWPE, ~0.7 wt % uniform vitamin E concentration, gamma sterilization (25-40 kGy)). Please note that both samples were obtained from uniformly cross-linked UHMWPEs which were then machined into the aging samples and the irradiated surfaces were not used.

There was high oxidation (average oxidation index>0.2) in vitamin E-blended and irradiated UHMWPEs after 6 and 14 days of aging (high and low pro-oxidant concentration, respectively) whereas in the irradiated, vitamin E-diffused, sterilized UHMWPEs (low and high pro-oxidant concentration both), the oxidation levels were below 0.2 after 30 days of aging (see FIG. 17). These results demonstrated that the irradiated, vitamin E-diffused, gamma sterilized UHMWPE had higher oxidation resistance that 0.1 wt % vitamin E-blended UHMWPE, which was irradiated to 120 kGy. We attributed this difference to the larger amount of vitamin E in the diffused UHMWPE.

Figure 18:
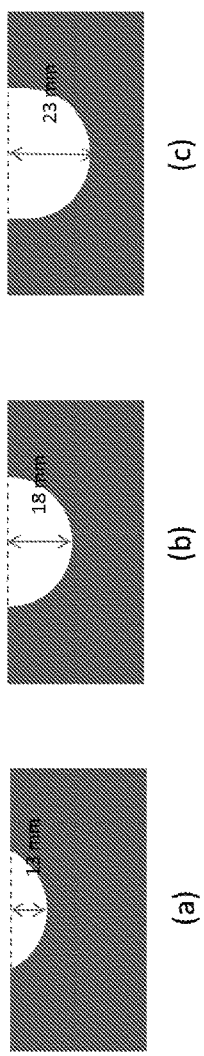
FIG. 18 shows the cross-sectional schematic view of curved vitamin E-blended UHMWPE surfaces exposed to irradiation.

Example 10. Low Energy Irradiation of Implant Preforms Stabilized by Antioxidant Medical grade UHMWPE resin flakes blended with 0.1 or 0.2 wt % vitamin E were consolidated by compression molding into cylindrical pucks (diameter 66 mm, length 56 mm; PPD Meditech, Waterville, Canada). Implant preforms were machined out of these pucks such that there was a curved surface intended to be an articular surface or could be machined further slightly into an articular surface. Three sets of surfaces were machined; a 'shallow surface', where the articular surface was part of a hemisphere (radius 18 mm) with a distance of 13 mm from the surface at the apex (see FIG. 18a), a 'flush surface', where the articular surface was a complete hemisphere with a radius of 18 mm (see FIG. 18b), and a 'deep surface', where the articular surface was a hemisphere (radius 18 mm) indented from the surface such that the apex was 23 mm from the surface (see FIG. 18c).

Figure 19:
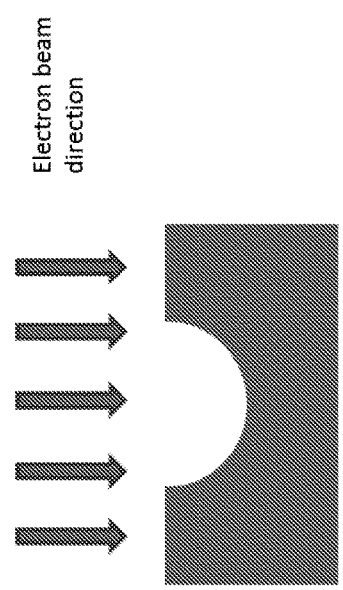
FIG. 19 is a schematic view of the curved surfaces with respect to the electron beam direction. The widening in the beam was assumed negligible. The schematic figures were drawn to provide an approximation of the processes described and were not meant to be taken as precise.

The curved surfaces were exposed to irradiation as schematically shown in FIG. 19. The irradiation was performed with electron beam energy of 0.8 MeV to 150 kGy at about 5 kGy/pass.

Figure 20:
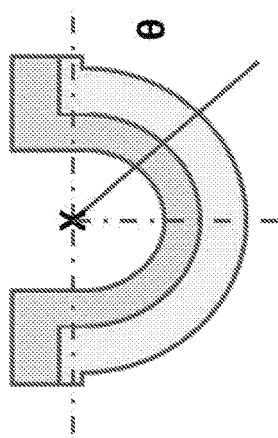
FIG. 20 is a schematic depiction of a thin section from a 'deep surface' puck irradiated by low energy electron beams. The surface depth exposed to irradiation is approximately depicted in the darker color and the bulk not exposed to irradiation was depicted approximately in the lighter color.

The analysis was done as follows: The blocks were cut in half along the length. A 150 micron-thick inner surface was microtomed (see FIG. 20) and analyzed by FTIR. Spectra were collected as an average of 32 scans from the irradiated surface towards the backside at 100-500 micron intervals. A transvinylene index was calculated by taking the area under the absorbance peak at 965 cm$^{-1}$ (950 to 980 cm$^{-1}$) and normalizing it to a crystalline peak of polyethylene at an absorbance of 1895 cm$^{-1}$ (1850 to 1985 cm$^{-1}$) after subtracting the corresponding baselines. The analysis was performed at θ=0, and 90° as depicted in FIG. 20 with θ=0° being at the apex.

Figure 21:
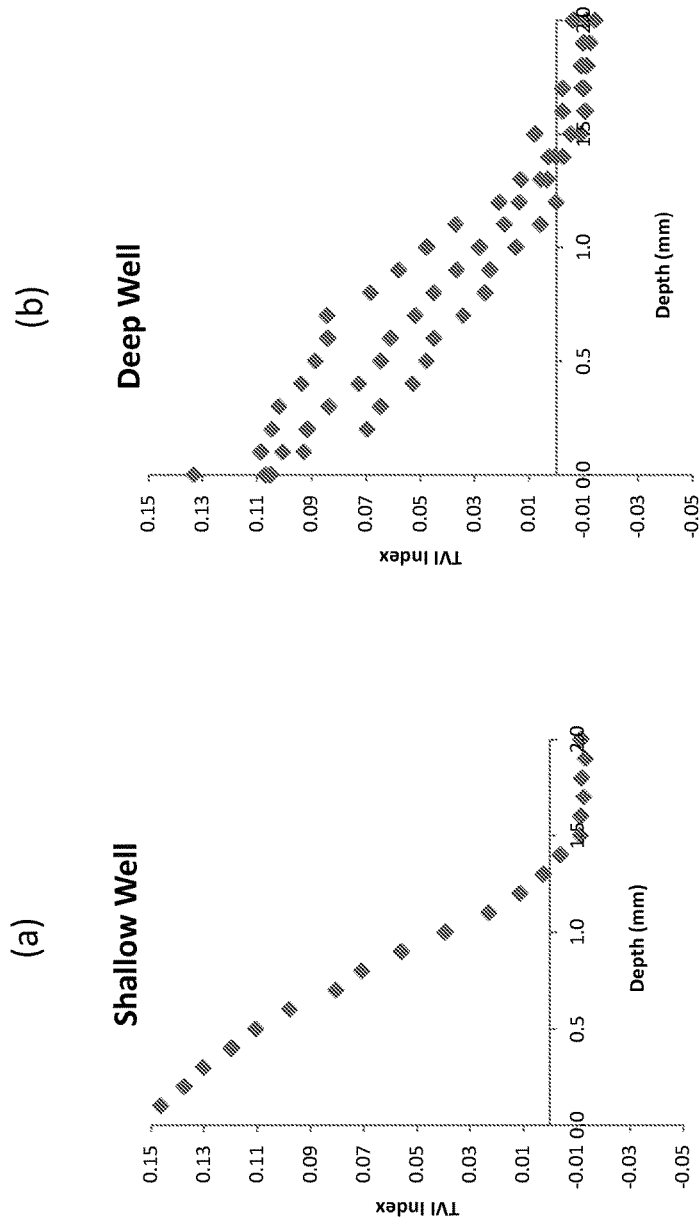
FIG. 21 shows the transvinylene index as a function of depth and angle of incidence of the beam at the surface for 0.1 wt % vitamin E blended pucks with 'shallow surface' (a) and with 'deep surface' (b).

The penetration depth of the beam at the apex was similar in shallow and deep well curved surfaces (see FIGS. 21a and b); however the surface value of the TVI, and presumably the cross-link density was higher for the shallow surface than for the deep surfaces. These results suggested that low energy irradiation was feasible for curved surfaces of antioxidant-containing medical implant preforms. These results also suggested that if the articular surfaces were recessed from the incident beam, the energy and/or power of the beam may have to be increased such that the scattering of the electrons due to the walls above the articular surface could be compensated for a given radiation dose. Additionally, the dose could be increased to achieve the same purpose.

Example 11. Irradiation Using an Alignment Cradle

Figure 22:
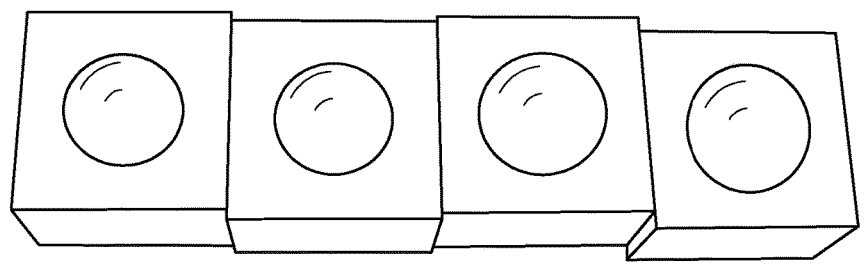
FIG. 22 shows two samples each of rectangular blocks with hemispherical recess (on the left—34 mm. inner diameter; on the right—38 mm. inner diameter).
Figure 23:
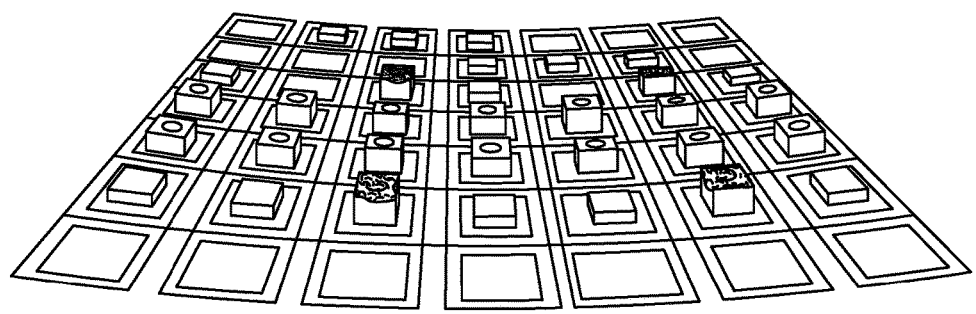
FIG. 23 shows a custom-made irradiation 'cradle'. The samples in the center were at an average alpha angle with the horizontal (see FIG. 7) of 0.3±0.0°, whereas those to the right were 3.0±0.1°, 5.7±0.1° and 8.4±0.1°, respectively. Those to the left had a beta angle with the horizontal (see FIG. 7) of 2.4±0.0°, 5.1±0.1° and 7.9±0.1°, respectively.

Medical grade GUR1020 UHMWPE was machined into rectangular blocks with hemispherical recess (n=6 with an inner diameter of 34 mm and n=6 with an inner diameter of 38 mm; see FIG. 22). Also, some rectangular blocks with flat surfaces were machined out of 0.1 wt % vitamin E blended GUR 1020 UHMWPE (60×60×20 mm). A cradle was constructed such that the divergent beam was normal to the tangent of the hemisphere at the dome as a realization of that described in FIG. 7 (see FIG. 23). The samples were positioned on the cradle as shown in FIG. 24.

Electron beam irradiation was performed using electrons with 1.7 MeV at a specified distance from the scanning horn window up to 150 kGy at about 25 kGy/pass. Some flat samples were irradiated to 160 kGy and some were irradiated to 170 kGy at about 10 kGy/pass for the remaining passes (see FIG. 24).

The blocks were cut; a 150 microns-thick inner surface was microtomed and analyzed by FTIR. Spectra were collected as an average of 32 scans from the edge of the thin film that corresponded to the irradiated surface towards the edge of the thin film that corresponded to the backside at 100-500 micron intervals. A transvinylene index (TVI) was calculated by taking the area under the absorbance peak at 965 cm$^{-1}$ (950 to 980 cm$^{-1}$) and normalizing it to a crystalline peak of polyethylene at an absorbance of 1895 cm$^{-1}$ (1850 to 1985 cm$^{-1}$) after subtracting the baselines.

Figure 25:
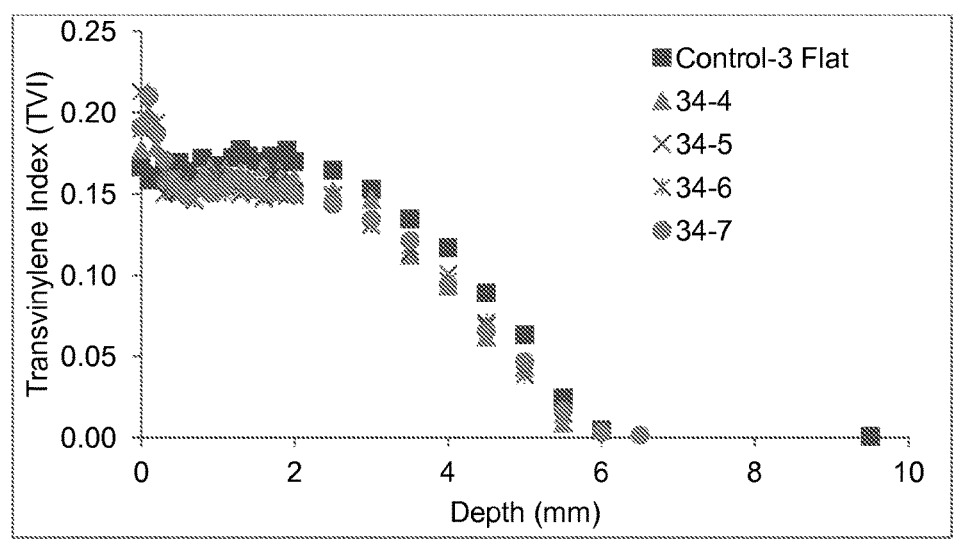
FIG. 25 shows the transvinylene index profiles from the irradiated surface into the depth of the samples for the flat control at alpha angle of 0°, the hemispherical recess sample with 34 mm. inner diameter at alpha angle of 0.3°, hemispherical recess sample with 34 mm. inner diameter at alpha angle of 3.0°, hemispherical recess sample with 34 mm. inner diameter at alpha angle of 5.7°, and hemispherical recess sample with 34 mm. inner diameter at alpha angle of 8.4°.
Figure 26:
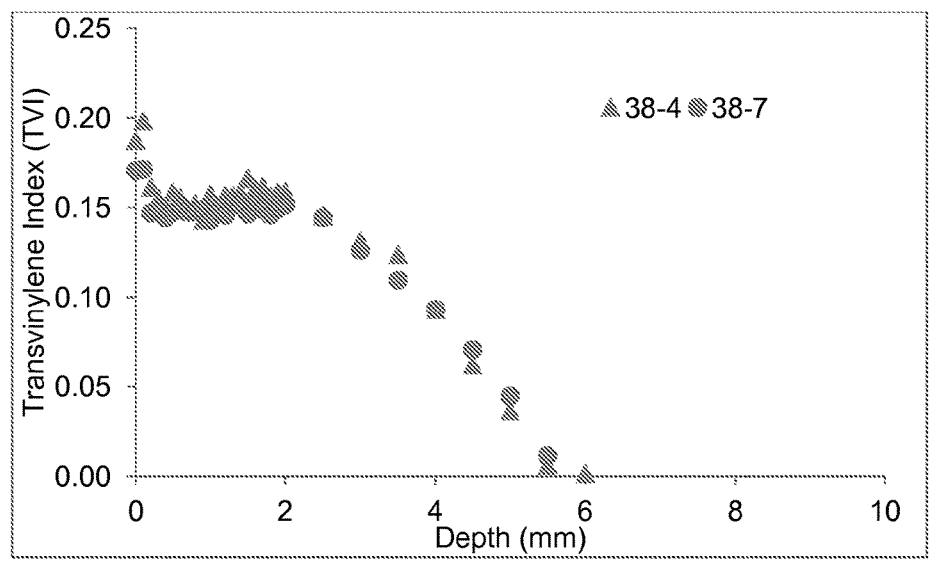
FIG. 26 shows the transvinylene index profiles from the irradiated surface into the depth of the samples for the flat control at alpha angle of 0°, the hemispherical recess sample with 38 mm. inner diameter at alpha angle of 0.3°, and hemispherical recess sample with 38 mm. inner diameter at alpha angle of 8.4°.

The TVI profiles of the hemispherical recessed samples with 34 mm inner diameter at the apex/dome to that of the flat control samples irradiated at the same angle with respect to the beam (see FIG. 25) showed that the cross-linked surface depth and the penetration depth for these samples were the same. Also, the comparison of the TVI profiles of the hemispherical recessed samples with 34 mm inner diameter at the apex/dome irradiated at different alpha angles on the irradiation 'cradle' showed that their profiles were substantially the same. This result was similar for the hemispherical recessed sample with 38 mm inner diameter (see FIG. 26).

Cylindrical pins (9 mm diameter×13 mm length, n=2 each) were machined from the 0.1 wt % vitamin E blended UHMWPE rectangular blocks irradiated to 150, 160 and 170 kGy (E-2, E-4 and E-9 in FIG. 24, respectively) with the irradiated surface as the wear surface. Another set of samples were irradiated from the same blocks with their wear surfaces at 1 mm below the surface by machining away 1 mm from the irradiated surface. Wear testing was done on a custom-designed bidirectional pin-on-disc (POD) tester in undiluted bovine serum. The pins were tested at 2 Hz under a peak load of 440 lbs for 1.2 million cycles (MC). They were weighed and the wear was determined gravimetrically at 500,000 cycles and every 157,000 cycles after that. Wear rate was determined by a linear regression of weight loss as a number of cycles from 500,000 cycles to 1.2 million cycles.

The wear rate of the 150 kGy irradiated 0.1 wt % vitamin E blended UHMWPE was 0.60±0.11 mg/MC at the surface and 0.40±0.12 mg/MC. The wear rate of the 160 kGy irradiated 0.1 wt % vitamin E blended UHMWPE was 0.47±0.09 mg/MC at the surface and 0.43 mg/MC. The wear rate of the 170 kGy irradiated 0.1 wt % vitamin E blended UHMWPE was 0.65±0.11 mg/MC at the surface and 0.36±0.01 mg/MC.

Example 12. Irradiation Using Metal Wool

Figure 27:
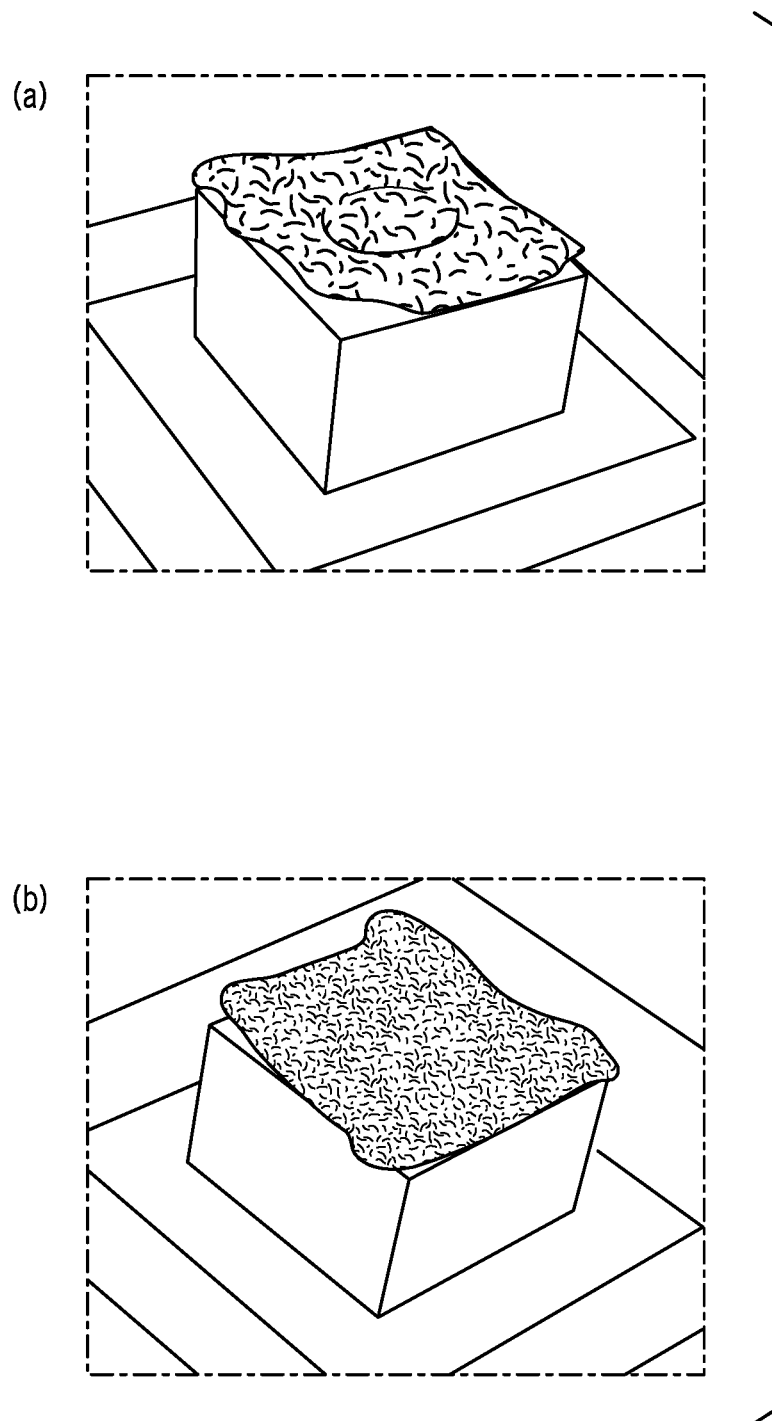
FIG. 27 shows the configurations of steel wool on hemispherical recessed samples; conforming to the surface (a) and flat in-line with the top surface (b).

Medical grade GUR1020 UHMWPE was machined into rectangular blocks with hemispherical recess (n=6 with an inner diameter of 34 mm and n=6 with an inner diameter of 38 mm). A cradle was constructed such that the divergent beam was normal to the tangent of the hemisphere at the dome (see FIGS. 7 and 23). Two samples of each size were covered with steel wool (grade 0000) either conforming to the recess (see FIG. 27a) or in line with the top of the sample (see FIG. 27b).

Electron beam irradiation was performed using electrons with 1.7 MeV at a specified distance from the scanning horn window up to 150 kGy at about 25 kGy/pass.

Example 13. Irradiation Schemes Using Metal Wool

Medical grade GUR1020 and GUR 1050 UHMWPE are machined into rectangular blocks with hemispherical recess (inner diameter of 34 mm and inner diameter of 38 mm). A cradle is constructed such that the divergent beam was normal to the tangent of the hemisphere at the dome (see FIGS. 7 and 23). Two samples of each size are covered with steel wool (grade 0000, grade 000, grade 00, grade 0, grade 1, grade 2, grade 3, or grade 4) either conforming to the recess (see FIG. 27a) or in line with the top of the sample (see FIG. 27b). Two samples of each size in these configurations are also covered with steel wool of these grades with 1 layer, 2 layers, 3 layers, 4 layers, 5 layers, or 6 layers of wool.

Electron beam irradiation is performed using electrons with 1.7 MeV at a specified distance from the scanning horn window at around 150 kGy, 175 kGy, 200 kGy, 225 kGy, 250 kGy, 275 kGy, or 300 kGy (two samples of each kind) at about 25 kGy/pass.

Each reference identified in the present application is herein incorporated by reference in its entirety.

While present inventive concepts have been described with reference to particular embodiments, those of ordinary skill in the art will appreciate that various substitutions and/or other alterations may be made to the embodiments without departing from the spirit of present inventive concepts.

Accordingly, the foregoing description is meant to be exemplary, and does not limit the scope of present inventive concepts.

A number of examples have been described herein. Nevertheless, it should be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the present inventive concepts.

What is claimed is:

1. A method of making a wear and oxidation resistant medical implant, the method comprising:
   (a) blending a polymeric material with one or more antioxidant(s);
   (b) consolidating the blended polymeric material into a medical implant preform;
   (c) irradiating the medical implant preform with low energy electrons at below 2 MeV with the desired surfaces exposed to the beam;
   (d) machining the medical implant preform into a medical implant; and
   (e) packaging and sterilizing the medical implant,
   wherein step (c) comprises irradiating the medical implant preform with an electron scattering device comprising fibers in contact with or close to the surface to be irradiated.

2. The method of claim 1 further comprising annealing the medical implant preform after step (c).

3. The method of claim 1, wherein the antioxidant used in blending in step (a) is vitamin E.

4. The method according to claim 1, wherein the material is pre-heated to an elevated temperature before irradiation such that the material is irradiated between 100° C. and 130° C.

5. The method according to claim 1, wherein the antioxidant concentration in the blend is 0.1 wt % to 5 wt %.

6. The method according to claim 1, wherein the irradiation dose is in the range of about 25 kGy to about 150 kGy.

7. The method according to claim 1, wherein the radiation dose rate is between about 1 kGy/pass to 50 kGy/pass.

8. The method according to claim 1, wherein the sterilization is a gamma sterilization.

9. A method of making a wear and oxidation resistant medical implant, the method comprising:
   (a) blending a polymeric material with one or more antioxidant(s);
   (b) consolidating the blended polymeric material into a medical implant preform;
   (c) irradiating the medical implant preform with low energy electrons at below 2 MeV with the desired surfaces exposed to the beam;
   (d) machining the medical implant preform into a medical implant; and
   (e) packaging and sterilizing the medical implant,
   wherein step (c) comprises irradiating the medical implant preform with an electron scattering device comprising metallic fibers or metallic wool or metallic brushes.

10. The method according to claim 1, wherein the electron scattering device is situated within a millimeter of intended surfaces to be irradiated.

11. The method according to claim 1, wherein the electron scattering device is situated within thirty centimeters of intended surfaces to be irradiated.

12. The method according to claim 1, wherein the polymeric materials comprises ultrahigh molecular weight polyethylene, and the antioxidant used in step (a) is vitamin E.

13. A method of making a wear and oxidation resistant medical implant, the method comprising:
   (a) blending a polymeric material with one or more antioxidant(s);
   (b) consolidating the blended polymeric material into a medical implant;
   (c) irradiating the medical implant preform with low energy electrons at below 2 MeV with desired surfaces exposed to a beam with an electron scattering device; and
   (d) packaging and sterilizing the medical implant,
   wherein the electron scattering device comprises fibers in contact with or close to the surface to be irradiated.

14. The method of claim 13 further comprising annealing the medical implant preform after step (c).

15. The method of claim 13, wherein the antioxidant used in blending in step (a) is vitamin E.

16. The method according to claim 13, wherein the material is pre-heated to an elevated temperature before irradiation such that the material is irradiated between 100° C. and 130° C.

17. The method according to claim 13, wherein the antioxidant concentration in the blend is 0.1 wt % to 5 wt %.

18. The method according to claim 13, wherein the irradiation dose is in the range of about 25 kGy to about 150 kGy.

19. The method according to claim 13, wherein the radiation dose rate is between about 1 kGy/pass to 50 kGy/pass.

20. The method according to claim 13, wherein the sterilization is a gamma sterilization.

21. A method of making a wear and oxidation resistant medical implant, the method comprising:
   (a) blending a polymeric material with one or more antioxidant(s);
   (b) consolidating the blended polymeric material into a medical implant;
   (c) irradiating the medical implant preform with low energy electrons at below 2 MeV with desired surfaces exposed to a beam with an electron scattering device; and
   (d) packaging and sterilizing the medical implant,
   wherein the electron scattering device comprises metallic fibers or metallic wool or metallic brushes.

22. The method according to claim 13, wherein the electron scattering device is situated within a millimeter of intended surfaces to be irradiated.

23. The method according to claim 13, wherein the electron scattering device is situated within thirty centimeters of intended surfaces to be irradiated.

24. The method according to claim 13, wherein the polymeric materials comprises ultrahigh molecular weight polyethylene, and the antioxidant used in step (a) is vitamin E.

25. A method of making a wear and oxidation resistant medical implant, the method comprising:
   (a) blending a polymeric material with one or more antioxidant(s);
   (b) consolidating the blended polymeric material into a medical implant preform;
   (c) irradiating the medical implant preform with low energy electrons at below 2 MeV with desired surfaces exposed to the beam;
   (d) doping the medical implant preform with one or more antioxidant(s); and
   (e) machining the medical implant preform into a medical implant, wherein step (c) comprises irradiating the medical implant preform with an electron scattering device comprising fibers in contact with or close to the surface to be irradiated.

26. The method of claim 25 further comprising annealing the medical implant preform after step (c).

27. The method of claim 25, wherein the antioxidant used in blending in step (a) and doping in step (d) is vitamin E.

28. The method according to claim 25, wherein the material is pre-heated to an elevated temperature before irradiation such that the material is irradiated between 100° C. and 130° C.

29. The method according to claim 25, wherein the antioxidant concentration in the blend is 0.1 wt % to 5 wt %.

30. The method according to claim 25, wherein the irradiation dose is in the range of about 25 kGy to about 150 kGy.

31. The method according to claim 25, wherein the radiation dose rate is between about 1 kGy/pass to 50 kGy/pass.

32. A method of making a wear and oxidation resistant medical implant, the method comprising:
(a) blending a polymeric material with one or more antioxidant(s);
(b) consolidating the blended polymeric material into a medical implant preform;
(c) irradiating the medical implant preform with low energy electrons at below 2 MeV with desired surfaces exposed to the beam with an electron scattering device;
(d) doping the medical implant preform with one or more antioxidant(s); and
(e) machining the medical implant preform into a medical implant,
wherein the electron scattering device comprises metallic fibers or metallic wool or metallic brushes.

33. The method according to claim 25, wherein the electron scattering device is situated within a millimeter of intended surfaces to be irradiated.

34. The method according to claim 25, wherein the electron scattering device is situated within thirty centimeters of intended surfaces to be irradiated.

35. The method according to claim 25, wherein the polymeric materials comprises ultrahigh molecular weight polyethylene, and the antioxidant used in step (a) is vitamin E.

* * * * *